United States Patent [19]

Bürk et al.

[11] Patent Number: 5,221,734
[45] Date of Patent: Jun. 22, 1993

[54] PROCESS FOR PREPARING A POLYPEPTIDE GROWTH FACTOR FOR MILK

[75] Inventors: Robert R. Bürk, Bottmingen; David Cox, Himmelried, both of Switzerland

[73] Assignee: Ciba-Geigy Corporation, Ardsley, N.Y.

[21] Appl. No.: 852,834

[22] Filed: Mar. 16, 1992

Related U.S. Application Data

[63] Continuation of Ser. No. 250,290, Sep. 28, 1988, abandoned.

[30] Foreign Application Priority Data

Oct. 1, 1987 [GB] United Kingdom ............... 8723094

[51] Int. Cl.$^5$ .................... C07K 3/02; C07K 15/06
[52] U.S. Cl. .................... 530/399; 530/416; 530/417
[58] Field of Search ............... 530/397, 412, 416, 350, 530/351, 397, 417; 514/21

[56] References Cited

U.S. PATENT DOCUMENTS

| | | | |
|---|---|---|---|
| 4,440,860 | 4/1984 | Klagsbrun | 435/240 |
| 4,627,982 | 12/1986 | Seyedin et al. | 424/95 |
| 4,774,228 | 9/1988 | Seyedin et al. | 514/21 |
| 4,774,322 | 9/1988 | Seyedin et al. | 530/353 |
| 5,043,431 | 8/1991 | Punger et al. | 530/399 |
| 5,047,510 | 9/1991 | Cone et al. | 530/399 |

FOREIGN PATENT DOCUMENTS

| | | |
|---|---|---|
| 169016 | 1/1986 | European Pat. Off. |
| 213776 | 3/1987 | European Pat. Off. |
| 268561 | 5/1988 | European Pat. Off. |
| 271211 | 6/1988 | European Pat. Off. |
| 8401106 | 3/1984 | PCT Int'l Appl. |
| 8805787 | 8/1988 | PCT Int'l Appl. |
| 8805788 | 8/1988 | PCT Int'l Appl. |

OTHER PUBLICATIONS

Pharmacia Separation News, vol. 13, No. 6, pp. 1-6 (1986).
Eur. J. Biochem 197:353 (1991), Cox et al.
J. Protein Chem. 10:565 (1991), Jin et al.
Shing et al., Mol. Endocrinol., vol. 1 No. 5 pp. 335-338 (1987).
Proc. Natl. Acad. Sci. vol. 82, pp. 3169-3172, May 1985 Zumstein et al.
Francis et al., Biochem. J., vol. 251 pp. 95-103 (1988, Apr.).
Brown et al., Biochem. J., vol. 219 pp. 609-617 (1984).
Delmas et al., PASCAL abstract, Univ. Lille 1, Th. doct.:biochim (1988).
Shing et al., Mol. Endocrinol., vol. 1 (5) pp. 335-338 (1987), (abstract).
Read et al., Journal of Developmental Physiology vol. 7 pp. 135-145 (1985).
Shing et al., Methods Enzymol vol. 146 pp. 42-48 (1987).
Shing et al., Endocrinology, vol. 115 pp. 273-292 (1984).
Klagsbrun, J. Cell Biology vol. 84 pp. 808-814 (1980).
Klagsbrun et al., J. of Supramolecular Structure vol. 11 pp. 349-359 (1979).
Klagsbrun, Proc. Natl. Acad. Sci. USA vol. 75 pp. 5057-5061 (1978).

(List continued on next page.)

*Primary Examiner*—Jeffrey E. Russel
*Attorney, Agent, or Firm*—Irving M. Fishman; Karen G. Kaiser

[57] ABSTRACT

A Milk Growth Factor (MGF) obtained from milk, methods for its isolation and purification from milk or milk products, pharmaceutical compositions, food compositions and cell growth media comprising the factor and the uses thereof for treating trauma in mammals, suppressing the immune response, treating cancer, stimulating growth of mammals and cell cultures.

5 Claims, 5 Drawing Sheets

OTHER PUBLICATIONS

Chou et al., The Jour. of Biol. Chem. vol. 254 No. 21 pp. 10588–10591 (1979).

Steimer et al., Jour. of Cell Biol. vol. 88 pp. 294–300 (1981).

Keller et al., Infection and Immunity vol. 32 No. 2 pp. 632–636 (1981).

Wrann et al., The EMBO Journal vol. 6 No. 6 pp. 1633–1636 (1987).

Ristow, Proc. Natl. Acad. Sci. USA vol. 83 pp. 5531–5533 (1986).

Marquardt et al., The Journal of Biological Chem. vol. 262 No 25 pp. 12127–12131 (1987).

Holley et al., Proc. Natl. Acad. Sci. USA vol. 75 No. 4 pp. 1864–1866 (1978).

Holley et al., Proc. Natl. Acad. Sci. USA vol. 77, No. 10 pp. 5989–5992 (1980).

Hanks et al., Proc. Natl. Acad. Sci. USA vol. 85 pp. 79–82 (1988).

Cheifetz et al., Cell vol. 48 pp. 409–415 (1987).

Ikeda et al., Biochemistry vol. 26 pp. 2406–2410 (1987).

Tucker et al., Science vol. 226 pp. 705–707 (1984).

Cheifetz et al., Abstracts of the 26th Harden Conference of the Biochemical Soc. (Sep. 1986).

Seyedin et al., Jour. of Biol. Chem. vol. 262 No. 5 pp. 1946–1949 (1987).

Burk, Control Mechanisms in Animal Cells pp. 245–257 Raven press New York (1980).

Burk, Proc. Natl. Acad. Sci. USA vol. 70, pp. 369–372 (1973).

Martin et al., The EMBO Journal vol. 6 No. 12 pp. 3673–3677 (1987).

PROCESS FOR PREPARING A POLYPEPTIDE GROWTH FACTOR FOR MILK

This application is a continuation of application Ser. No. 250,290, filed Sep. 28, 1988, now abandoned.

BACKGROUND OF THE INVENTION

1. Field of the invention

This invention relates to the isolation and purification of a polypeptide growth factor from milk, to synergistic mixtures and pharmaceutical, cosmetic and food compositions comprising it, and to the uses thereof for the promotion and acceleration of wound healing and tissue repair, the suppression of immune responses, the treatment of cancer and the stimulation of growth of mammals and cell cultures. This polypeptide will be referred to herein as Milk Growth Factor (MGF).

2. Background of the invention and prior art

Growth factors can be defined as polypeptides that stimulate cell growth and proliferation at very low concentrations through specific, high-affinity cell surface receptors. This action produces other intracellular signals which result in nutrient uptake, DNA synthesis and cell division, and which eventually lead to tissue growth. Growth factors have been found in a variety of body tissues and fluids, in both the adult and the embryo, and are now believed to be released by most, if not all, cells in culture (see review by Goustin, A. S. et al. (1986), Cancer Research, 46, 1015.) As such, growth factors do not usually function in an endocrine manner but presumably diffuse over short distances through inter-cellular spaces, or act in an autocrine or paracrine fashion.

Milk is one such body fluid that contains factors which stimulate cell growth in culture. A variety of cell types including epithelial cells, normal and transformed fibroblasts, smooth muscle cells and chondrocytes have been shown to proliferate in blood serum-free, milk-supplemented culture medium (Klagsbrun, M. (1980), J.Cell Biol., 84, 808; Steimer, K. S. and Klagsbrun, M. (1981), J.Cell Biol., 88, 294; Sereni, A. and Baserga, R. (1981), Cell Biol. Int. Rep., 5, 338). Such activity has been found in milk and colostrum (the milk expressed during the first few days post partum) obtained from human (Klagsbrun, M. (1978) Proc. Natl. Acad. Sci. USA, 75, 5057.) and bovine sources (Steimer, K. S. et al. (1981), J.Cell Physiol., 109, 223.) In recent years, a number of growth factors have been isolated from milk and purified to homogeneity in an attempt to characterise their structure and biological function.

One of the earliest and better characterised growth factors is Epidermal Growth Factor (EGF), a polypeptide with a molecular weight of about 6 kd and which has growth and proliferative effects on a variety of cells and tissues both in vitro and in vivo. EGF has also been shown to be the major growth promoting agent in human milk (Carpenter, G. (1980), Science, 210, 198; Petrides, P. E. et al., (1985), FEBS Letters 187, 89), bovine milk (Yagi, H. et al., (1986), Acta.Scand.Paed. 75, 233), and murine milk (Beardmore, J. M. and Richards, R. C., (1983) J.Endocrinol. 96, 287).

Two factors with the name of Mammary Derived Growth Factor (MDGF) have also been isolated from milk. Human MDGF-I is a reducing agent-sensitive polypeptide with a molecular weight of about 62 kd and an isoelectric point (pI) of 4.8 (Bano, M. et al., (1985) J.Biol.Chem. 260, 5745). At picomolar levels it stimulates the growth of mammary cells and enhances their levels of collagen production. MDGF-II is also sensitive to disulphide reducing agents, however, has a lower molecular weight of about 17 kd and a pI of 4.4 (Zwiebel, J. A. et al., (1986), Cancer Research, 46, 933). Using high ionic strength eluting buffers, MDGF-II can be resolved from human EGF on a TSK-3000SW gel filtration column although it still competes with radiolabelled $^{125}$I-EGF for binding to the EGF receptor on A431 human epidermoid carcinoma cell membranes. MDGF-II also stimulates the anchorage independant growth of Normal Rat Kidney (NRK) cells in soft agar, the defining characteristic of a Transforming Growth Factor (TGF), and it seems probable that MDGF-II belongs to the TGF-$\alpha$ family since molecules of the larger TGF-$\beta$ type do not bind to the EGF receptor. It has also been reported that human milk and bovine milk contain different sets of growth factors. Shing and Klagsbrun (1984, Endocrinol., 115, 273) have isolated three species of growth factor from human milk, which have been named HMGF-I, HMGF-II and HMGF-III. HMGF-III appears to constitute over 75% of the total growth factor activity of human milk as measured by DNA synthesis. HMGF-III has a molecular weight of about 6 kd, a pI of 4.4-4.7, and is insensitive to treatment with reducing agents. Comparative studies have suggested that this molecule is probably EGF. Using the same separation procedures, these workers also showed that bovine colostrum lacks this molecule although it does have a major growth factor component which has a molecular weight of 30-35 kd and is inactivated by treatment with reducing agents. This so-called Bovine Colostrum Growth Factor (BCGF) is biochemically similar to HMGF-II, another molecule which accounts for approximately 20% of the total growth factor activity of human milk.

A Colony Stimulating Factor (CSF) which stimulates in vitro bone marrow cell proliferation and which causes the differentiation of Colony Forming Granulocytic Macrophage pro-genitor cells (CFU-GM) has also been isolated from human milk (Sinha, S. K. and Yunis, A. A. (1983), Biochem. Biophys. Res.Comm. 114, 797). This factor, which is absent in bovine milk or colostrum, is also insensitive to the action of reducing agents. Gel filtration and isoelectric focussing experiments have indicated that it is biochemically distinct from other CSF's and has a molecular weight of 240-250 kd and a pI of 4.4-4.9.

There are a number of other growth factors or related factors which are to be mentioned in connecton with the present invention which were derived from sources other than milk.

Human platelet, human placenta and bovine kidney derived TGF-$\beta$ molecules are described in International Patent Application WO84/01106 and EP 0128849. Patent No. EP-0169016 and U.S. Pat. No. 4,627,982 reports the partial purification of two proteins from bovine demineralized bone (CIF-A and CIF-B), which are co-factors for inducing cartilage formation. CIF-B (TGF-$\beta$2) has been found to inhibit inflammatory cell function in vivo (EP 213 776) and to have an inhibiting effect in vitro on the proliferation of tumour cells (EP 271 211). Both of these so-called Cartilage Inducing Factors are active when combined with EGF in the TGF-$\beta$ assay. One of their factors (CIF-A) has an N-terminal sequence which is identical over the first thirty amino acids to that of human placenta derived TGF-$\beta$, but which is significantly different to that of CIF-B [see also review articles by Sporn, M. (1986), Science, 233, 532, and Massagué, J., Cell 49, 437–438 (1987)].

CIF-B [Seyedin, S. M. et al., (1987) J.Biol.Chem. 262; 1946; EP 169016] is similar, if not identical to two other recently reported growth factors. Cheifetz, S. et al., (1987) *Cell*, 48: 409) have described a factor which they have isolated from porcine platelets and which they have designated TGF-β2, since it has a different-N-terminal amino acid sequence to the original porcine TGF-β (now being designated TGF-β1 in the scientific literature) isolated from the same source. More recently Wrann, M. et al., (1987) EMBO J. 6: 1633) have isolated a factor from human glioblastoma cells which is immunosuppressive for T-lymphocytes and is designated G-TsF. CIF-B, TGF-β2 and G-TsF have the same amino acid sequence at the N-terminal up to amino acid 19. CIF-B and TGF-β2 have the same molecular weight of about 26 kd, whereas G-TsF has a molecular weight of 12.5 kd. A human TGF type β2 (hTGF-β2) with a molecular weight of 24 kd, and consisting of two disulfide-linked apparently identical polypeptide chains, isolated from the tamoxifen-supplemented human prostatic adenocarcinoma cell line,, has been described by Marquardt, H. et al., J.Biol.Chem., 262, 12127–12131 (1987) and Ikeda, T. et al., Biochem. 26, 2406–2410 (1987).

A growth inhibitor BSC-1 GI, named polyergin, obtained from BSC-1 African green monkey kidney cells, was identified and purified by R. W. Holley et al., Proc. Natl. Acad. Sci. USA, Vol. 75, pp. 1864–1866 (1978), and R. W. Holley et al., ibid. Vol. 77, pp. 5989–5992 (1980). It was shown by R. F. Tucker et al., Science Vol. 226, 705–707 (1984) to have nearly identical biological activity with TGF-β1 and by H. J. Ristow, ibid. Vol. 83, pp. 5531–5533 (1986) to be a strong inhibitor of thymocytic proliferation. The amino acid sequence of BSC-1 GI, as deduced from the cDNA fron a BSC-1 cell cDNA library, was recently found to be identical to the amino acid sequence of TGF-β2 [S. K. Hanks et al., Proc. Natl. Sci. USA, Vol. 85, pp. 79–82 (1988)].

These growth factors hitherto have not been shown to be present in milk.

Although a number of polypeptide growth factors have already been isolated, characterised and cloned, there have been few studies on the activity of these materials in vivo, mainly because of the relatively small amounts available for such experiments. An important indication area for the potential application of the present growth factor is the enhancement of wound healing. Despite the many preparations available for the treatment of wounds there are still large numbers of patients, particularly the elderly, with wounds (including trauma, burns, decubitus and diabetic ulcers) that either heal slowly or fail to heal at all. Such patients present a significant worthwhile target group for a pharmaceutical preparation which would promote and accelerate the wound healing process. Types of small wounds are those in the mouth, especially of the gum, and also those caused e.g. by a razor blade in the face or other parts of the body surface. Stimulation of the growth of mammals, such as in the treatment of dwarfism, and of cell cultures in vitro are also possibilities for the use of the present growth factor.

Surprisingly the present growth factor contains also suppressing activites on certain types of cells, namely those of the immune system and also of cancer cells.

It is quite obvious that a continuous need for the treatment of these indications exists.

Object of the present invention

The object of the present invention is to make available a polypeptide growth factor found in milk which is named "Milk Growth Factor" or "MGF", a process for its enrichment, recovery and purification, pharmaceutical, cosmetic and food compositions comprising it, and their uses for promoting cell proliferation, migration and tissue repair in mammals.

Further objects are to suppress the immune responses and the proliferation of cancer cells by administration of the present growth factor.

A still further object is the stimulation of the growth and proliferation of cells in vitro.

A further object is to provide synergistic mixtures comprising the growth factor and an activating agent.

DETAILED DISCLOSURE OF THE INVENTION

This invention concerns a Milk Growth Factor (MGF) in enriched and pure form characterised in that it is obtainable from milk or milk products, having a molecular weight of about 25 kd as determined by SDS-PAGE and an isoelectric point of between pI 9.0 and 10.5, or a salt thereof.

By the term "Milk Growth Factor" (MGF) as used herein is intended any enriched or purified, also partially purified state of this factor. This enrichment can be from about $10^3$ fold to over $10^7$ fold and the factor may have a purity up to 100%. The MGF is essentially free of other growth factors which may be found in milk and having a lower or higher molecular weight and a different pI, such as EGF or HMGF III (6 kd), MDGFI (62 kd), MDGFII (17 kd), BCGF (30-35 kd) or CSF (240-250 kd).

In particular the present invention concerns the MGF from bovine milk in its essentially purified form having the following amino acid composition

| Amino Acid | Amino Acids/Mole | |
|---|---|---|
| | a) | b) |
| ASP + ASN | 21.10 | 20 |
| GLU + GLN | 24.68 | 24 |
| SER | 19.00 | 18 |
| THR | 10.02 | 10 |
| GLY | 10.62 | 10 |
| ALA | 14.64 | 14 |
| ARG | 9.50 | 10 |
| PRO | 12.92 | 12 |
| VAL | 10.68 | 10 |
| MET | 0.16 | 2 |
| ILE | 11.04 | 10 |
| LEU | 22.40 | 22 |
| TRP | not determined | |
| PHE | 7.78 | 8 |
| CYS | 11.16 | 12 |
| LYS | 16.14 | 16 |
| HIS | 5.84 | 6 |
| TYR | 13.38 | 14 |

[a): moles amino acid per mol peptide; b): rounded to give amino acid residues per mol peptide]

and the following N-terminal amino acid sequence 1           5           10
Ala—Leu—Asp—Ala—Ala—Tyr—Cys—Phe—Arg—Asn—

15                 19
—Val—Gln—Asp—Asn—Cys—Cys—$X^{17}$—$X^{18}$—Pro, wherein $X^{17}$ and $X^{18}$ are undetermined amino acids, or a salt thereof.

The molecular weight is determined by Sodium Dodecyl Sulphate-Polyacrylamide Gel Electrophoresis (SDS-PAGE) according to the method of Laemmli, U. K. (1970) Nature, 227, 680. The isoelectric point is determined by the method outlined by Bürk, R. R. (1980) in "Control Mechanisms in Animal Cells" pp. 245–257, Raven Press, New York. The cationic nature of this polypeptide is due to the presence of basic amino acid groups such as arginine, lysine and histidine. MGF is a heat-stable, acid-stable polypeptide which is sensitive to reducing agents such as mercaptoethanol, dithiothreitol and the salts thereof. Treatment of MGF with such agents indicates that the molecule is composed of two similar or identical sub-units, each of approximately 12.5 kd in size, which are presumably held together by one or more cystein disulfide bonds and which become cleaved on treatment with the said agents.

The observation that MGF does not appear to be species specific in its action in promoting cell migration and proliferation supports the hypothesis that the said molecule is highly conserved among the different mammalian species and is therefore expected to be substantially homologous with other molecules of this family.

In this respect the term 'substantially homologous' as applied to a polypeptide, refers to those molecules whether native, synthetic or recombinantly produced, regardless of species or origin, that have the same amino acid sequence as MGF, and polypeptides of substantially homologous but different amino acid sequence, whose differences do not affect cross species activity in an adverse fashion. Accordingly the polypeptide of this invention, MGF, originally isolated from cow's milk, may well be derived from milks of diverse mammalian origin or made by recombinant DNA technology. Cow milk is a preferred native source of MGF since it is readily available in large quantities thereby unrestricting the amount of factor that can be produced using the outlined purification procedures.

For analytical purposes samples of homogenous MGF (50–100 pmol) were taken to dryness and hydrolysed in sealed, evacuated tubes at 150° C. for 2 hours in 100 μl constant boiling 6N HCl containing 0.1% liquid phenol. Half-cysteine and methionine were determined by performic acid oxidation followed by acid hydrolysis. Analyses of o-phthalaldehyde derivatives of the amino acids were done on a modified amino acid analyzer equipped with a fluorimeter and computing integrator.

The number of amino acid residues per mole of MGF is based on an apparent molecular weight of 25000 Dalton.

For amino-terminal sequence analysis, approximately 500 picomoles ($M_r$ 25,000) of MGF were reduced and S-carboxymethylated with dithiothreitol and iodo-[$^{14}$C]acetic acid in the presence of 6M guanidine-HCl in 1M Tris-HCl buffer, pH 8.4. Excess reagents were separated from carboxymethylated protein by HPLC on a 5 micron 50×4.6 mm column eluted with a gradient of 0–90% acetonitrile (1% per min) in 0.1% TFA. Overall recovery of the procedure was 96%, based on estimating the amount of protein by amino acid analysis using fluoresceine detection.

Automated Edman degradation was performed on about 500 pmoles ($M_r$ 12,500) of the S-carboxymethylated protein with a gas-phase sequencer. PHT-amino acids were identified using an HPLC system. Initial yield was about 30% and repetitive yield about 90%. The results indicate that the sequence of at least the first nineteen N-terminal amino acids of each of the two subunits of MGF are identical and confirm the observations of a single protein band of the reduced form of MGF by SDS-PAGE.

Analysis of bovine MGF by SDS-PAGE suggests that some of the disulphide bonds are interchain.

In view of its basic groups the new growth factor can form acid addition salts with inorganic or organic acids. For the purpose of purification water and/or alcohol insoluble salts are envisaged, such as the tetraphenylborate, Ca-, Al-, Zn-salts and the like.

For pharmaceutical purposes pharmaceutically acceptable salts are contemplated, such as water soluble metal or ammonium salts, especially alkali metal or alkaline earth metal salts, e.g. sodium salts, potassium salt, magnesium salt or calcium salt, or ammonium salts with ammonia or a suitable organic amine. Preferred are acid addition salts with an inorganic acid, for example hydrochloric acid, sulfuric acid, or phosphoric acid, or with an organic acid, especially an organic carbonic or sulfonic acid, for example a lower alkane carboxylic or dicarboxylic acid, e.g. formic or acetic acid, citric acid, trifluoroacetic and the like.

The MGF of the present invention is further defined by its biological properties. The growth promoting activities of MGF in its various states of purification are determined according to the assay described by Bürk, R. R. (1973) Proc.Natl.Acad.Sci.USA 70: 369, which measures the number of normal Balb/C 3T3 fibroblast cells (or strains derived therefrom) that migrate into a 'wounded' monolayer culture of the said cells, in the presence of a serum-free medium containing MGF, as compared to the number of cells that migrate in the absence of MGF or any other known polypeptide growth factor.

Dose response experiments using the said method have shown that concentrations of the completely purified MGF as low as 40±35 picogrammes per milliliter of culture medium are sufficient to elicit 50% of the maximal migratory response. This concentration of MGF elicits also 50% of the maximal migratory response in the said assay when a human skin epithelial cell line (NCTC 2544) is used as the indicator cell type.

MGF is further characterised by its stimulating activity on cellular DNA synthesis and cell division apparent in the said monolayer cultures when observed under the light microscope. This activity was quantified by either:

a) counting the number of cell nuclei, in any given field of view, in cultures of the said cells grown in the presence of serum-free medium containing MGF, as compared to the number of cell nuclei counted, in any given field, in cultures grown in the absence of MGF or any other known polypeptide growth factor.

b) measuring the amount of radio-labelled [$^3$H]-thymidine uptake in cultures of the said cells grown in the presence of serum-free medium containing MGF, as compared to the amount of [$^3$H]-thymidine uptake in cultures grown in the absence of MGF or any other known polypeptide growth factor.

The growth promoting activity of MGF is only a property of the 25 kd dimeric form of the molecule. This activity can be recovered in the supernatant eluates from gel slices containing the said dimer, following SDS-PAGE and overnight elution in 50 millimolar formic acid under an atmosphere of nitrogen. No activity could be recovered in eluates from the gel slices containing the 12.5 kd monomer form. The growth promoting activity of MGF is also apparent when tested in cell cultures of a mammalian origin and type other than the said Balb/c 3T3 fibroblast type, suggesting that the growth promoting response to MGF derived from bovine milk is not species specific in its nature.

MGF is further characterised in that it acts synergistically in the presence of EGF. This synergism is found in an assay for the in vitro induction of Anchorage Independant Growth of Normal Rat Kidney (NRK) cells in soft agar (Roberts, A. B. et al., (1981) Proc.Natl.Acad. Sci.USA 78: 5339). This assay is sometimes referred to as the Transforming Growth Factor type Beta (TGF-$\beta$) assay since TGF-$\beta$ (unlike TGF-$\alpha$) does not compete with EGF for binding to membrane receptor sites, but does require the occupancy of their other "activating agent" receptor sites for the induction of cell colonies. In this regard, the presence in milk of proteins having such a synergistic action with EGF in the said assay has not been previously reported. MGF alone is not sufficient to induce the formation of large colonies of NRK cells in soft agar but will only do so in the presence of murine EGF. In the presence of a concentration of EGF (5 ng ml$^{-1}$) which alone is insufficient to cause a noticeable effect in this assay, MGF induces large colony formation when added over a concentration range of from 0.1 to 500 ng ml$^{-1}$.

Although picomolar concentrations of MGF are enough to promote the migration and proliferation of normal Balb/C 3T3 fibroblast cells in vitro, a synergistic response occurs in the presence of murine EGF. In the assay described by Bürk, R. R. (1973) Proc.Natl.Acad.Sci.USA 70: 369, the maximal migratory response to MGF (over a concentration range of from 10 to 100 pg ml$^{-1}$) in the presence of 3.16 ng/ml murine EGF has been shown to be up to 30 times higher than in the absence of EGF.

The invention concerns also a combination, especially a synergistic combination, of MGF and any polypeptide, which exerts an agonistic effect by binding to EGF receptor. Such a polypeptide is, besides EGF itself, for example, TGF-$\alpha$. Such a combination is especially useful for treating deeper wounds, such as caused by heavy accidents or surgery. Preferred is an equimolar combination of MGF and EGF.

The invention concerns also a process for the preparation of a Milk Growth Factor (MGF) or a salt thereof, characterised in that MGF is recovered from milk or any milk product containing it and when required transforming an obtainable free MGF into a salt or an obtainable salt into the free MGF.

The present growth factor is recovered by conventional methods from any source of fresh milk or milk product containing it. Preferred sources of MGF are especially milk or milk products, in particular of bovids, e.g. cows, goats, sheep and the like. Another source is commercially available milk powder, such as dried skimmed milk powder.

More specifically, the growth factor is recovered by subjecting the milk source to various chromatographic methods, especially such as cation exchange chromatography, hydrophobic interaction chromatography, size exclusion chromatography, polyacrylamide gel electrophoresis and/or, if necessary further purification processes. Advantageously a protease inhibitor, such as phenyl methanesulfonyl fluoride, is added to the MGF containing source.

The process for isolating MGF from fresh bovine milk is characterised e.g. by cation-exchange chromatography, hydrophobic interaction chromatography, and size-exclusion chromatography steps using a combination of both low pressure and high pressure techniques. Sample fractions collected from each subsequent separation step, and which show biological activity in the said cell migration assay on Balb/c 3T3 cells, are pooled and forwarded to the next separation step. Sample material from each of the pooled fractions are subjected to a dose response analysis (using the same bioassay method on the said cells), thereby allowing for estimation of the volume of material required to elicit 50% of the maximal migratory response. This said volume is hereby defined as 'one unit' and using this value, together with the values for the volume of material in each active pool, the purification yields, recoveries and specific activity at each step of the process can be calculated. Homogeneity of the pure MGF from the final purification step is demonstrated by:

i) Constant specific activity
ii) Migration as a single band of approximately 25-26kd following SDS-PAGE.
iii) Constant Amino Acid Composition
iv) Constant Amino Acid Sequence Analysis.

In particular, the recovering of MGF is achieved by treating diluted milk containing the growth factor or an aqueous suspension of the milk powder with a cation-exchange resin, washing the resin loaded with the factor with a buffer system of pH 7.0 sodium dihydrogen phosphate (10 mM), eluting the factor from the resin with a buffer system consisting of potassium dihydrogen phosphate (20 mM) in 40% ethanol, of pH 7.6, subjecting it, in particular in the form of an acid addition salt thereof, to hydrophobic interaction chromatography, size-exclusion chromatography and polyacrylamide gel electrophoresis, and if desired further purification processes and, if desired transforming the obtained growth factor in the form of the base into a salt, or transforming the growth factor obtained in the form of a salt into the free base or into another salt.

Before the chromatography the milk or milk powder may be freed from fat and other unpolar material, e.g. by extracting with an unpolar organic solvent, such as methylenechloride, or in the case of the milk powder with acetone. Milk is diluted in distilled water in a milk:water ratio of about 1:3 to 1:10, preferably about 1:4, by volume.

The milk powder is suspended in distilled water in a powder:water proportion of about 1 to 5 to 1 to 20, preferably about 1 to 10, by weight.

For the cation exchange chromatography any suitable cation exchange resin may be used, for example Bio Rad AG 50W series resins, Amberlite IR series resins, Zeocarb 22S, Diaion SK series resins, Dowex AG 50W series resins. Ion exchangers in the form of exchangeable countergroups bound to solid matrix supports (in the form of discs or cartridges) may also be used, for example Zetaprep 3P series cation exchangers.

A preferred cation exchange resin is Dowex AG 50W X2 50-100 mesh. The resin may be washed before use with acetone, ethanol and/or water. After loading with a cation, for example an alkali metal cation such as sodium or potassium, by treatment with the corresponding metal hydroxide, e.g. alkali metal hydroxide, the resin is washed neutral and is then equilibrated to a pH 7.0 with a suitable low ionic strength buffer, preferably a sodium dihydrogen phosphate buffer (10 mM). The fresh or reconstituted milk is adjusted to the same pH with the same alkali metal hydroxide and is then brought into contact with the resin. The loaded resin is washed with the same buffer of pH 7.0 until the washing is free of polypeptide, i.e. until the base line of the optical density at 280 nm is reached. The desired growth factor is then eluted with an alkali metal salt aqueous buffer solution of high ionic strength in particular with potassium acetate (700 mM) in the presence of 40% ethanol, at pH 7.6. The fractions exhibiting the desired activity are pooled and, if desired, concentrated by evaporation. About 10% of the initial activity is obtained with a 1000 fold increase in specific activity.

The pooled fractions are subjected to hydrophobic interaction chromatography on a resin consisting of an uncharged matrix which supports interactive hydrophobic groups. Any suitable resin may be used, for example phenyl sepharose or octyl sepharose. A preferred hydrophobic interaction resin is phenyl sepharose CL-4B.

Before use the phenyl sepharose is regenerated by consecutive washings with an alcohol, e.g. with n-butanol and ethanol, and then with water. The pooled fractions from the Dowex chromatography are applied to the phenyl sepharose column by directly stirring the resin, overnight, into the pool. The resin is then loaded onto the column which is washed with 0.6M ammonium acetate pH 5.0 followed by a step gradient with a rising amount of ethanol, e.g. from 28% to 40% in the same solvent pH 5.0 which is sufficient to elute the desired activity.

The active fractions of the phenyl sepharose hydrophobic interaction chromatography step are pooled, and either lyophilised and redissolved in a small amount of a high ionic strength buffer solution, for example 2M ammonium acetate at pH 5.5, or directly applied to a butyl-polyol hydrophobic interaction chromatography column which forms the first active component of a high performance liquid chromatography (HPLC) system. The column is washed with the same buffer, followed by a linear gradient with a rising amount of ethanol, for example 20–25%, which is sufficient to elute the desired activity.

The active fractions of the butyl-polyol hydrophobic interaction chromatography step are pooled, admixed with a larger, preferably equal volume of the same solvent buffer, namely 2M ammonium acetate at pH 5.5, and applied to an octyl-polyol hydrophobic interaction chromatography column which forms the second active component of an HPLC system. The column is washed with the same buffer followed by a linear gradient with a rising amount of ethanol, for example 40–45%, which is sufficient to elute the desired activity.

The active fractions of the octyl-polyol hydrophobic step are pooled, lyophilised and redissolved in a small volume, preferably 100 μl, of a buffer solution consisting of 7 parts 60% ethanol to 3 parts 2M ammonium acetate pH 5.5, and subjected to size-exclusion chromatography on a TSK G2000 SW column which forms the third active component of an HPLC system. The elution process is performed under isocratic elution conditions, using the same buffer solution, and the fractions containing the activity are pooled, lyophilised and stored at −20° C. until further use.

The obtained growth factor migrates as a single band with a molecular weight of about 25–26kd according to SDS-PAGE, and may be from about 95% up to 100% pure.

If required, further purification of the growth factor can be achieved by one or more of above chromatographic methods or other methods applied in the art of polypeptide purification, such as countercurrent distribution, electrofocussing, chromatofocussing, dialysis, salt and solvent precipitation, adsorption with other gels, cellulose ion exchange chromatography, electrophoresis chromatography on porous glass beads, chromatography on immobilized zinc chelate HPLC, and the like. An obtained free MGF, that is in the form of an inner salt, may be treated with an acid or a base to form the desired salt or an obtained salt may be transformed into the free base or into another salt by methods known in the art, especially with aid of ion exchange resins loaded with the desired anion and the like.

The presence of the growth factor in the various fractions during its purification can be checked by measuring the optical density at 280 nm and especially by determining the various properties by which it is characterised. A preferred method is the determination of the cell migration stimulating properties of the fractions according to the Migration Assay of Bürk, R.R. (1973) Proc.Natl.Acad.Sci.USA 70: 370. $2 \times 10^5$ 3T3-B cells (a derivative of Balb/C 3T3 cells clone A31) are seeded in 2.5 ml of Dulbeccos modified Eagle's medium containing 10% calf serum in 35 mm plastic petri dishes (Nunc). After 3 days at 37° C., a wound is made in the confluent cell monolayer by pressing a sterile razor blade onto the bottom of the dish to cut the cell sheet and to mark a 'start line'.

The blade is gently moved to the side to remove part of this sheet. The fluid medium and the cell debris is removed by suction and replaced by 2.5 ml of Eagle's medium without serum, followed by an appropriate amount of the fraction containing the growth factor to be tested. After 22 hours at 37° C. room temperature the cells are fixed and stained with Leishmann's solution. Migration activity is defined as the number of cells crossing 1 mm of the 'start line' made by the razor blade.

The present invention concerns further a pharmaceutical composition comprising an effective amount of a Milk Growth Factor or a pharmaceutically acceptable salt thereof in dosage unit form.

Such composition is in the form of infusion solutions or preparations for parenteral, for example intramuscular or intravenous, oral, or especially for local, i.e. topical, administration, respectively. The solutions are preferably isotonic aqueous solutions or suspensions which can be prepared before use, for example from lyophilised preparations which contain the active ingredient alone or together with a pharmaceutically acceptable carrier. Solutions for parenteral use are usually aqueous solutions. They are prepared in conventional manner and may contain in addition to the active ingredient physiological saline, a stabilizer, such as human serum albumin, amino acids, such as arginine or glycine, and a carbohydrate, such as glucose, mannose, dextran or hydroxyethyl starch. The pH may be adjusted with a buffer, e.g. a phosphate, succinate or an amino acid to about 4.5 to 7. Usually the vials are filled with the solution and lyophilized for longer storage.

Mouth wash solutions are also prepared in conventional manner. They contain the active ingredient for example dissolved in water or aqueous ethanol, e.g. of about 30 to 60%, and may contain usual additives, such as a polyethyleneglycol glycerin, and an etherical oil, e.g. mint oil, for improving the taste. The pharmaceutical preparations for topical use comprise powders, cremes, including toothpastes, chewing gums, lotions, tinctures and the like, which are likewise prepared in a conventional manner. Powders are conventionally consisting of talc and the active ingredient and optionally other additives, such as stabilizers and fragrances. Creams and ointments are of conventional nature and may comprise a stearate, such as sorbitan or polyoxyethylene sorbitan monostearate, an oleate, such as sorbitan trioleate, an alcohol, such as cetyl alcohol, or propylene glycol, a paraffin or microcristalline wax, such as lanolin, a powder, such a magnesium sulphate, or for a toothpaste a conventional cleansing powder, preservatives, and the like. Solid dosage forms for buccal or pharyngeal administration can be lozenges prepared using common pharmaceutical excipients e.g. a) diluents and lozenge bases such as surcrose, dextrose, lactose, mannitol or sorbitol, b) binders such as starch paste, gelatin, polyvinylpyrrolidone, hydroxypropyl methylcellulose, c) lubricants such as magnesium or calcium stearates, stearic acid, talc or hydrogenated vegetable oils and, if desired d) colorants, flavours, sweeteners etc.. Alternatively, pastilles made with a basis of gelatin and glycerol or a mixture of acacia and sugar can be used for slow dissolution in the mouth.

Solid dosage forms for oral ingestion by swallowing can be tablets or gelatin capsules. The active substance is formulated with appropriate common pharmaceutical excipients and additives e.g. for tablets a) diluents such as lactose, starch, cellulose, sorbitol, calcium phosphates or calcium sulphate, b) binders such as starch paste, gelatin, polyvinylpyrrolidone, hydroxypropyl methylcellulose or other suitable cellulose ethers, c) disintegrants such as starch, sodium starch glycolate, sodium carboxymethylcellulose, crospovidone, d) lubricants and glidants such as magnesium or calcium sterates, stearic acid, talc, colloidal silicon dioxide, hydrogenated vegetable oils and, if desired, e) surfactants such as sodium lauryl sulphate, colorants etc. Tablet cores may be provided with a suitable coating which may or may not be resistant to gastric fluid. The outer coats may be sugar-based or may constitute thin films based on cellulose ethers or acrylic resins. Sugar coats can be applied using concentrated sugar syrups and coating suspensions containing common coating ingredients such as talc, polyvinylpyrrolidone, polyethylene glycols and dyestuffs or pigments. Film-coats are preferentially applied as aqueous solutions or suspensions and may contain film-forming agents such as hydroxypropyl methylcellulose, plasticizers such as polyethylene glycol, antiadherents such as talc, colour pigments and opacifiers such as titanium dioxide and iron oxides. Enteric coatings are obtained with lacquer solutions of polymers which are insoluble in gastric fluid but soluble in intestinal fluid, e.g. cellulose acetate, phthalate or methacrylic acid copolymers in organic solvents.

Capsules are either made using fabricated hard gelatin shells to be filled with the drug formulation or using soft gelatin shells formed and sealed during the filling process from a mixture of gelatin and a softening agent such as glycerin or sorbitol. The hard gelatin capsules may contain powder mixtures formulated with diluents, lubricants and glidants as mentioned for tablets under a) and d) or may be granulates with ingredients similar to those used for compression into tablets and mentioned above under a)-d). Alternatively the hard gelatin capsules may contain liquids, pastes or solid masses with the active substance dissolved or dispersed in suitable liquids or semi-solid bases such as polyethylene glycols, fatty oils or polyoxyethylated glyceride derivatives, if required with thickening agents such as waxes or colloidal silicon dioxide and/or surfactants such as polysorbates. In soft capsules the active ingredient is preferably dissolved or suspended in suitable liquids such as fatty oils, paraffins or polyethlyene glycols. The active substance can also be incorporated into small pellets to constitute a multiple-unit dosage form for oral ingestion. Distribution of the drug among the pellets may be attained by spraying a solution or suspension onto the surface of prepared pellets or by forming pellets from a mixture containing the drug and appropriate diluents. For surface application, pellets may be commercially available non-pareil sugar spheres containing sugar and starch, or may be produced by extrusion and spheronisation using excipients such as microcrystalline cellulose and lactose wet massed with water. The latter process can be used to incorporate the drug within the pellets. Pellets may be coated with protective or release-regulating lacquers using polymers such as ethylcellulose, polymethacrylate resins, cellulose acetate phthalate etc., applied as solutions in organic solvents or as aqueous dispersions. The pellets can be filled into hard gelatin capsules or compressed into tablets together with appropriate tabletting excipients.

The compositions contain conventional adjuncts, for example preservatives, stabilisers, wetting agents and/or emulsifiers, solubilisers, salts for regulating the osmotic pressure and/or buffers. The present pharmaceutical compositions, which may, if desired, contain further pharmacologically valuable substances, are produced in a manner known per se, for example by means of conventional mixing, dissolving, lyophilising and/or sterilising processes, and contain from approximately 1 ng to 100 $\mu$g/g, especially from approximately 10 ng to 10 $\mu$g/g of preparation, and in the case of lyophilisates up to 100%, of the active ingredient.

The invention also concerns a method for producing a pharmaceutical composition characterised in that a pharmacologically active compound of the present invention is processed in a conventional manner, e.g. admixed with a pharmaceutically acceptable carrier.

The invention also concerns a toothpaste comprising an effective amount of MGF, or a pharmaceutically acceptable salt thereof, and a method for its preparation. The toothpaste is especially useful for prevention and/or treatment of wounds of the gums, e.g. periodontitis or gingivitis.

The invention also concerns a mouthwash comprising an effective amount of MGF, or a pharmaceutically acceptable salt thereof, and a method for its preparation. The mouthwash is useful for prevention and/or treatment of wounds in the mouth and throat, e.g. such which occur during periodontitis, gingivitis or inflammation of the throat.

The invention concerns also a cosmetic compositions comprising an effective amount of MGF, or a cosmetically acceptable salt thereof. The cosmetic composition may be similar to the topical pharmaceutical preparation, and in addition may contain fragrant compounds. Such compositions comprise conventional shaving soaps, foams, cremes and lotions.

The invention concerns also the use of the MGF for the preparation of a pharmaceutical composition, mouthwash solution, tooth paste and cosmetic preparation.

MGF is dual in character in that it on the one hand stimulates the proliferation of one type of body cells, namely fibroblasts and other mesenchymal cells, and on the other hand inhibits the proliferation of another type of body cells, namely tumour cells and cells of the immune system.

The new growth factor, optionally in the form of a salt, such as in particular a non-toxic pharmaceutical acid addition salt, optionally in form of a pharmaceutical formulation, is applied in an effective amount. By the from "effective amount" is intended an amount which exerts a significant healing or cosmetic effect, e.g. an amount which stimulates the desired cells to grow and which is not toxic to the cells. This amount can be determined e.g. by in vitro growth experiments. Due to the dual character of MGF, an "effective amount" is also such which to a significant extent inhibits the growth and proliferation of tumour cells and cells of the immune system. If human or veterinary use is intended, the amount has to be adjusted to the particular tissue to be treated, the mode of application, the severity of the disease, and the age and general condition of the host to be treated. In general, the dosages for adult humans will be in the range of about 0.1 to 1000 $\mu$g for both the growth stimulating and the inhibiting effect. Allergic reactions may be avoided by using the growth factor from the particular species to be treated, i.e. using the growth factor from human milk for treating human beings, from cow's milk for treating cattle, etc.

Clinical Uses of the Compositions of this Invention

The pharmaceutical compositions of this invention, whose active ingredients are MGF or MGF in combination with a suitable activating agent, preferably EGF, have a clinical use in the treatment of animals, particularly mammals, more particularly human beings, and, in the case of wound healing, most particularly of old human beings. Several results are presented to support this evidence in the Protocols I to VII.

The compositions of this invention promote cell migration and proliferation. Since wound healing involves both cell migration and cell proliferation patterns these in vitro findings become directly relevant to the in vivo wound healing process.

As important characteristic of the components of the compositions of this invention is that species-specific combinations are not required for their activity either in vitro or in vivo, i.e. MGF from one species, for example bovine, can be activated by an activating agent from another species, for example murine EGF. Furthermore, the cells whose migration and/or growth is being promoted, either in vitro or in vivo, may also be of a different species from the components of the composition, or of other types, such as fibroblast or epithelia (although it is considered that the growth promotion of these two said cell types will have the greatest medical utility.) The synergy of MGF with EGF suggests that skin is a suitable target. Prevention or treatment of bed sores (decubitus ulcers) is a preferred goal since they frequently occur in hospital patients, particularly geriatric and wheel chair patients. In elderly people the wound healing process is slower and this group of patients tends to show a higher incidence of wounds (not only decubitus and diabetic ulcers, but trauma, burns and the like) that either heal slowly or do not heal at all.

Two types of application of the compositions of this invention are proposed for both veterinary and, in particular, human medicine.

The first, and preferred application is a topical one for the promotion of surface wound healing, particularly in elderly human beings where the wound healing processes are noticeably slower. There are no limitations as to the type of wound that may be treated, and these include (but are not limited to): Surface ulcers including decubital (bed sore), diabetic, dental, oral, varicose and haemophiliac surface ulcers; burns (especially second and third degree); surgical incisions (including those of dental and cosmetic surgery); accidental wounds (including incisions, penetrations, lacerations and other traumata) and therapeutically induced wounds (including those induced during radiotherapy). When applied topically, the compositions may be combined with other ingredients, such as adjuvants, carriers, solubilizing agents and any other known, or as yet unknown, secondary growth factor(s). There are no limitations as to the nature of these ingredients except that they must be pharmaceutically and physiologically acceptable for administration and must not degrade the activity, or render harmfully toxic, the active ingredients of the compositions. When the compositions of this invention are applied to surface ulcers, burns, surgical or accidental wounds, the compositions are preferably in the form of a powder, gel, ointment, salve or irrigant, or they may be impregnated into transdermal patches, plasters and bandages, preferably in a liquid or semi-liquid form, or they may be incorporated into a tooth paste or a gum or resin for chewing.

The second application is a systemic one for the healing of internal wounds either following surgery, or damage to the tissues of the inner organs where surgery is either impossible or is not required. Again, there are no limitations as to the type of tissue or wound to be treated and these include (but are not limited to) deep surgical incisions to the inner organs and tissues; bone and cartilage (after fracture); gastric, duodenal and other intestinal ulcers. When applied systemically, the compositions of the invention may be formulated as liquids, pills, tablets, lozenges for enteral administration, or in liquid form for parenteral injection. For the treatment of internal incisions following surgery, they may be in the form of an irrigant, preferably in combination with a physiologically acceptable saline solution. Again, the active ingredients of the compositions may be combined with other ingredients such as adjuvants, carriers, solubilizing agents and any other known, or as yet unknown, secondary growth factor(s). There are no limitations as to the nature of these ingredients except that they must be pharmaceutically and physiologically acceptable for administration and must not degrade the activity, or render harmfully toxic, the active ingredients of these compositions.

The invention concerns also a method for preventing or treating mammalian trauma comprising administration of a pharmaceutical composition or also a cosmetic composition.

For healing the wounds the amount of active ingredient to be applied is not very critical. In general a daily amount of from about 0.1 to 10 $\mu$g MGF per 1 cm$^2$ of wound has already a significant healing effect. For internal use a higher amount should be applied depending on the mode of administration due to the dilution of the MGF in the body fluids. The safety for higher amounts is given by the fact that MGF is present in milk.

Surprisingly the MGF of the present invention has also broad spectrum immunosuppresive activities as evidenced in Protocols IV and V.

Accordingly, the invention concerns also a method for suppressing immune responses comprising administration of an immunosuppressively effective amount of MGF, or a pharmaceutically acceptable salt thereof.

The immunosuppressive effect of the present MGF can be used in organ transplantation operations or also to prevent and treat autoimmune diseases, such as inflammations.

Further, the MGF of the present invention has antitumor activities, e.g. against melanoma cells, as can be shown by the antiproliferative effects against melanoma cell line A 375 (Protocol VI) and human breast cancer cells (Protocol VII).

Accordingly, the invention concerns also a method for the treatment of cancer comprising administration of an antiproliferatively effective amount of MGF, or a pharmaceutically acceptable salt thereof.

The amount of activating agent required will depend upon the amount of MGF present in the relevant compositions of this invention, although experiments suggest that approximately equimolar amounts are preferred. Exact amounts of the active components, together with any extra ingredient of the compositions of this invention depends on the specific activity of the MGF and/or the activating agent, the disease to be treated, e.g. also on the size, nature and location of the wound. For topical application to surface wounds, including melanoma, MGF should be present in an amount of at least 1 nanogramme up to 1 milligramme per millilitre. Since the active components of this invention exert their effects by binding to receptor sites and are then utilized by the cells whose growth and migration are being stimulated, a continual or periodic re-application of the compositions is preferred.

Other uses of MGF

Whilst the major role of milk is clearly in the nutrition of the neonate, MGF may also have effects, not just at the local tissue level, but may promote the growth of the whole animal in a manner analogous to Human Growth Hormone (HGH). In this regard it is envisaged that the compositions of this invention may also be useful as food additives in raising young animals, for example, calves, lambs, foals, piglets, and chickens.

Thus the invention concerns further a food composition comprising a growth promoting amount of MGF or a salt thereof and a method of stimulating growth of a mammal comprising administering to the said animal a growth stimulating amount of a food composition, comprising a growth promoting amount of MGF or a salt thereof.

A further application is the use of MGF for the growth of culture cells which are difficult to grow under normal culture conditions, e.g. the SV40 virus transformed embryonic human fibroblast cell line WI-38 VA13. Additionally MGF can be used for growing certain cells in protein-poor or essentially protein-free media, permitting savings in serum used in the cell culture. Thus, as the test according to R. R. Bürk indicates, picomolar concentrations of about 1 to 1000 pM of the factor stimulate migration and growth of Balb/C 3T3 cells in serum free medium.

Accordingly the invention concerns also a cell growth medium essentially free of other proteins, comprising a growth promoting stimulating amount of a MGF or a salt thereof, and a method of stimulating cell growth in vitro in a medium essentially free of other proteins, comprising adding to said medium a growth stimulating amount of a MGF or a salt thereof.

SHORT DESCRIPTION OF THE FIGURES

The FIGS. 1 to 5 show the progress of the purification of MGF during various chromatographic steps. Recorded are for each fraction the absorbance by measuring the optical density (O.D.) at 280 nm, and the migration activity in the test of Bürk, R.R. (1973) Proc.-Natl.Acad.Sci. USA 70, 369.

The following examples serve to illustrate the present invention but should not be construed as a limitation thereof.

Example 1: Isolation of Milk Growth Factor from fresh bovine milk a) Cation-Exchange Chromatography

Dowex AG 50W X2 50-100 mesh resin (30 liter; H+ form) is loaded into a suitably sized chromatography column and washed firstly with 2-3 bed volumes of 1M sodium hydroxide in 50% ethanol followed by 3-6 bed volumes of distilled water. The resin is then equilibrated in the Na+ form) with 2-3 bed volumes of 0.01M sodium dihydrogen phosphate, pH 7.0. Fresh milk (250-400 l.) is diluted with 4 volumes of distilled water following the addition of 40 ml 0.1M phenylmethanesulfonyl fluoride (PMSF), a protease inhibitor, to the crude milk. The diluted milk solution is then pumped slowly through the column bed at 4° C., thereby allowing for absorption of the appropriately charged milk proteins to the resin.

Figure 1:
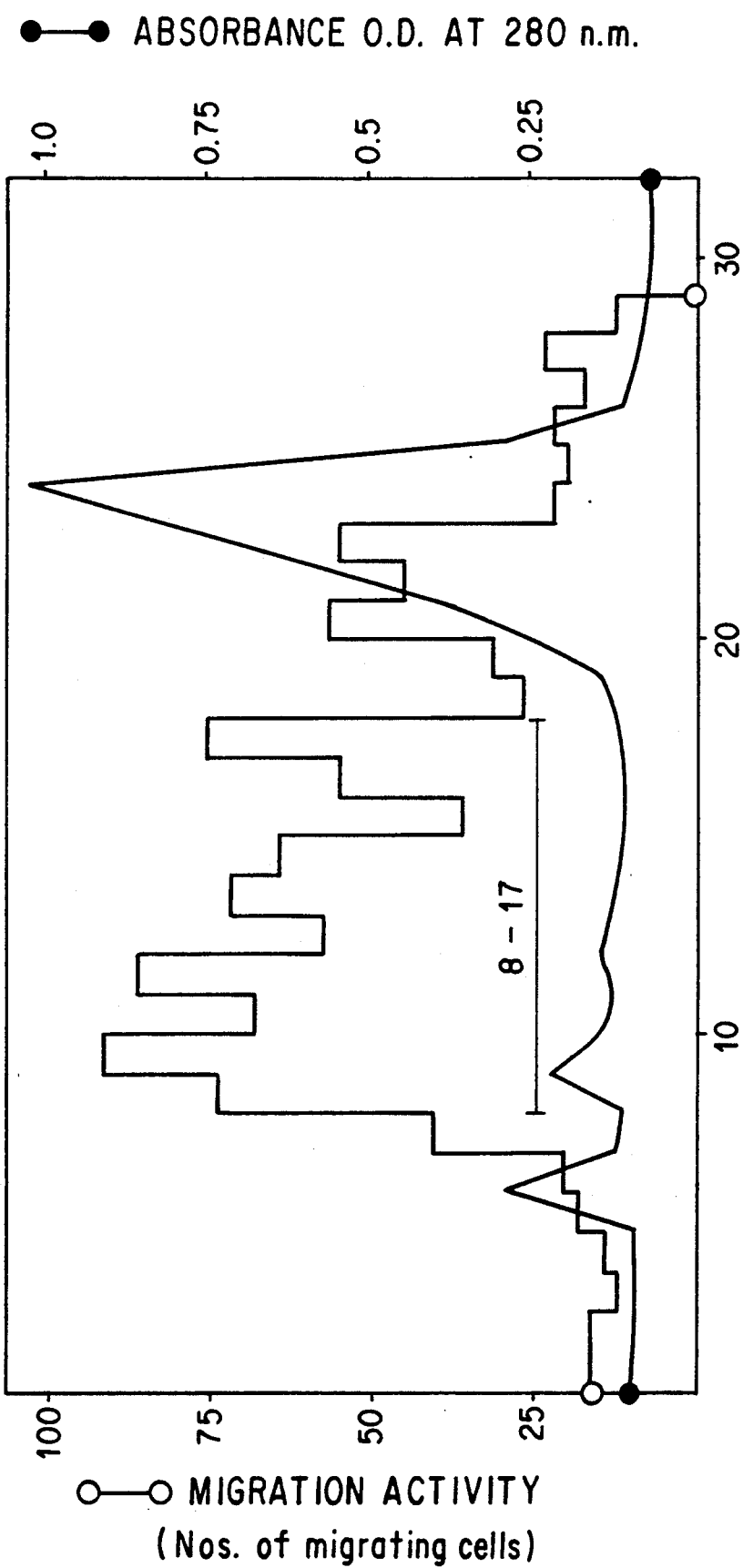
FIG. 1 represents the results of the Cation-Exchange Chromatography according to Example 1a)

After loading, the resin is washed with 1½ bed volumes of 0.01M sodium dihydrogen phosphate, pH 7.0. The column is then eluted with approximately 2½ bed volumes of 0.02M potassium dihydrogen phosphate and 0.7M potassium acetate in 40% ethanol, at pH 7.6 until the O.D. 280 nm returns to the baseline. Each fraction is immediately adjusted to pH 4.5-5.5 with acetic acid. The potassium acetate elutes a small peak with absorbance at 280 nm and which contains much of the desired activity. FIG. 1 represents the absorbance at 280 nm over the elution phase, together with the migration activity of the collected fractions. The active fractions (Nos. 8-17) are pooled, concentrated 2-3 fold by rotary evaporation, and stored at 4° until required.

b) Hydrophobic Interaction Chromatography I

Figure 2:
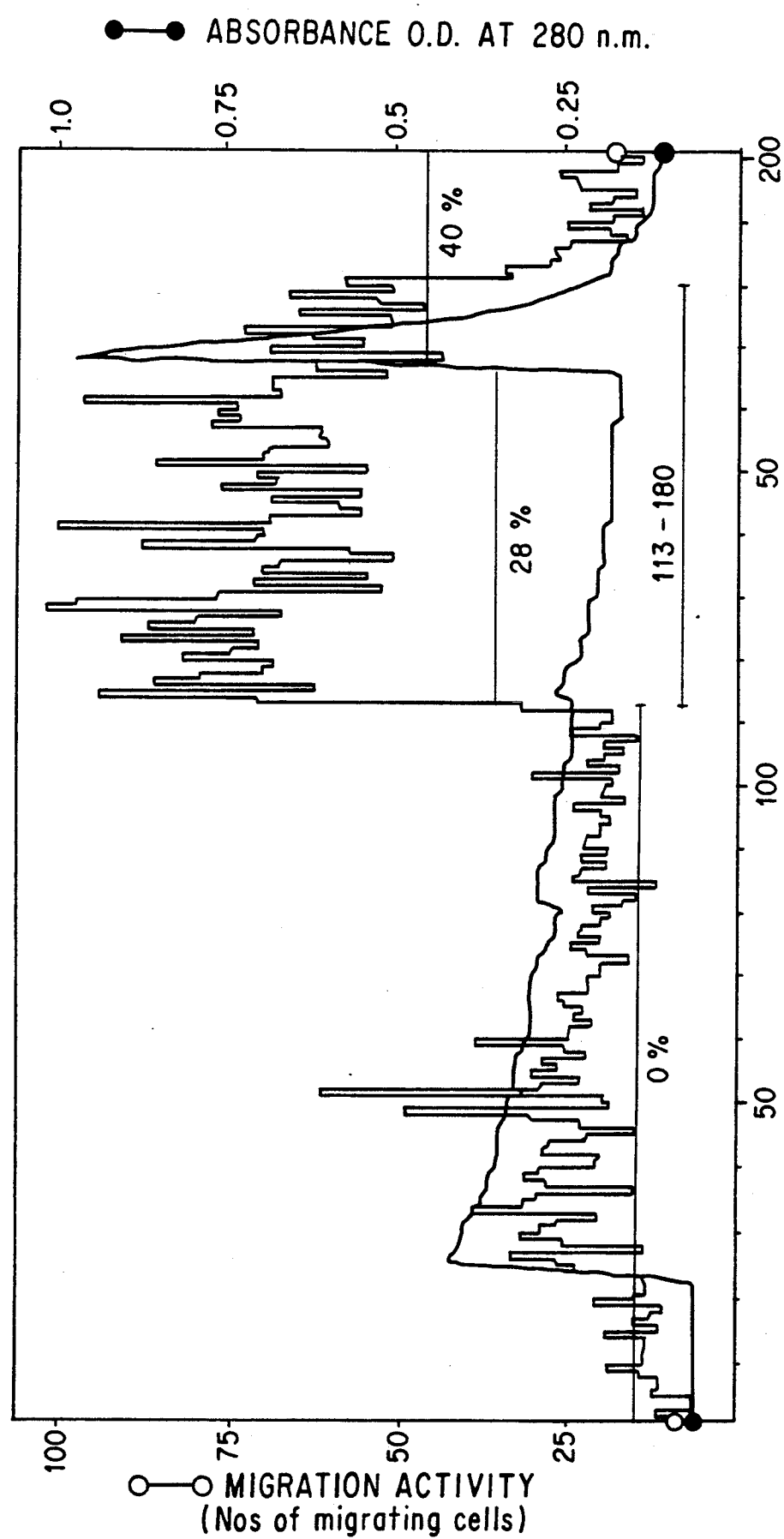
FIG. 2 represents the results of the Hydrophobic Interaction Chromatography I according to Example 1b)

Phenyl Sepharose CL 4B from Pharmacia is regenerated by washing with 1 column volume of n-butanol, 1 volume of ethanol and about 10 volumes of distilled water. The pool of the active fractions from paragraph a) (total volume usually 40-50 liters which may be reduced by rotary evaporation at reduced pressure) is adjusted to pH 5.0 with 1M ammonium hydroxide in a suitably sized vessel. Approximately 750 milliliters of Phenyl Sepharose CL 4B resin, as prepared above, is added to the vessel and the contents are stirred gently overnight at 4° C. The stirring is then stopped, the resin is allowed to settle and the supernatant material is carefully decanted and discarded. The resin is then transferred to a large sintered glass funnel and washed thoroughly with an amount of a buffer solution, consisting of 0.6M ammonium acetate, required so that the effluent is no longer opaque. The resin is then transferred to a suitably sized chromatography column and the loaded column is then washed with a further 2 volumes of 0.6M ammonium acetate, pH 5.0, followed by steps at 28% and 40% ethanol in 0.2M ammonium acetate, pH 5.0, which is sufficient to elute the desired activity. The 28% step may be ommitted to reduce the volume. FIG. 2 represents the absorbance at 280 nm over the elution phase, together with the migration activity of the collected fractions. The active fractions (Nos. 113-180) are pooled and stored at 4° C. until required.

c) Hydrophobic Interaction Chromatography II (HPLC)

Figure 3:
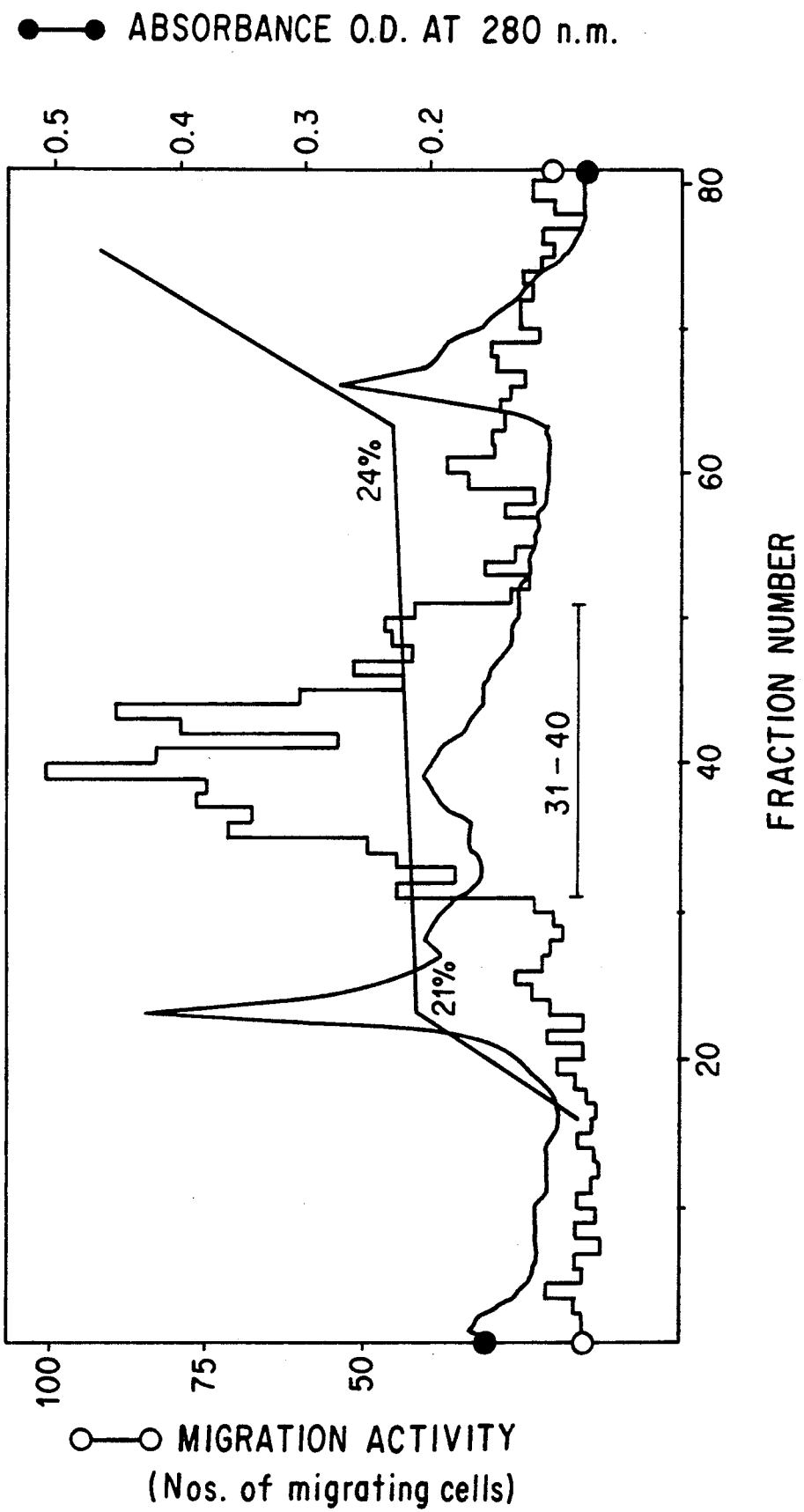
FIG. 3 represents the results of the Hydrophobic Interaction Chromatography II according to Example 1c)

The pool of the active fractions from paragraph b) (total volume usually 2-2.5 liters) is either lyophilised to dryness and redissolved in a small volume, usually 50 milliliters, of a mixture consisting of 7 parts 60% ethanol to 3 parts 2M ammonium acetate pH 5.0, or concentrated 3 to 10-fold by vacuum evaporation. To this is added a further 1-2 volumes of a buffer consisting of 2M ammonium acetate pH 5.5 and the solution is pumped onto a Butyl Polyol Si500 (10 μm pore size)) hydrophobic interaction chromatography column, at room temperature, at a flow rate of 1 milliliter per minute. The column is then washed with the same buffer solution followed by elution using a linear gradient with a rising amount of ethanol, in this example 21-24% over the flattened part of the gradient, which was sufficient to elute the desired activity. FIG. 3 represents the absorbance at 280 nm over the elution phase, together with the migration activity of the collected fractions. The active fractions (Nos. 31-40) are pooled and stored at −20° C. in a closed container to avoid evaporation until further use.

d) Hydrophobic Interaction Chromatography III (HPLC)

Figure 4:
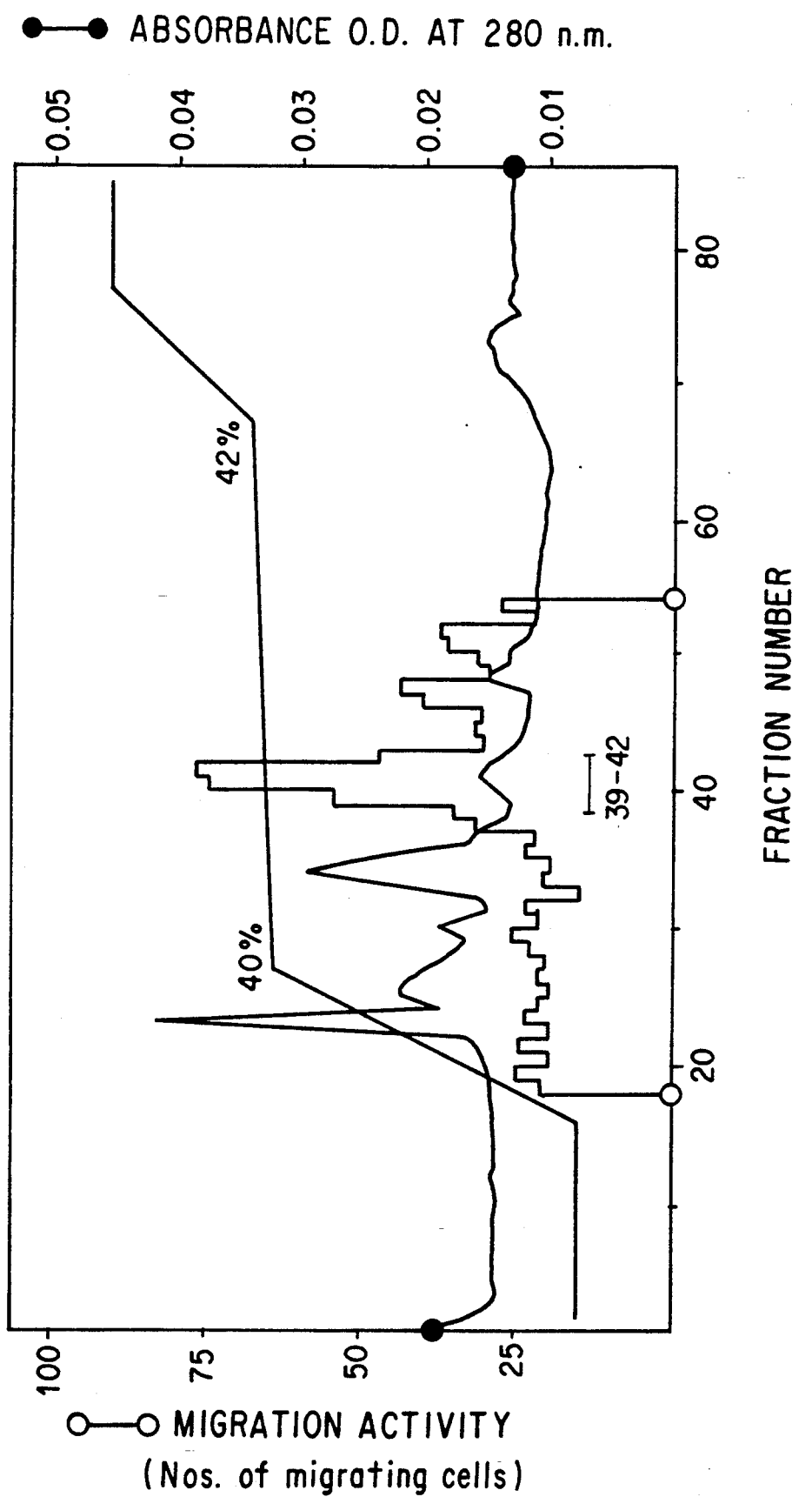
FIG. 4 represents the results of the Hydrophobic Interaction Chromatography III according to Example 1d)

The pool of the active fractions from paragraph c) (total volume usually 20-40 milliliters) is admixed with a equal volume of a buffer consisting of 2M ammonium acetate pH 5.5 and the solution is pumped onto an Octyl Polyol Si500 (10 μm pore size)) hydrophobic interaction chromatography column, at room temperature, at a flow rate of 1 milliliter per minute. The column is then washed with the same buffer followed by elution using a linear gradient with a rising amount of ethanol, in this example 40-42% over the flattened part of the gradient, which was sufficient to elute the desired activity. The column is finally stripped with repetitions of a 0-100% linear ethanol gradient. FIG. 4 represents the absorbance at 280 nm over the elution phase, together with the migration activity of the collected fractions. The active fractions (Nos. 39-42) are pooled and stored at −20° C. until required.

e) Size-Exclusion Chromatography (HPLC)

Figure 5:
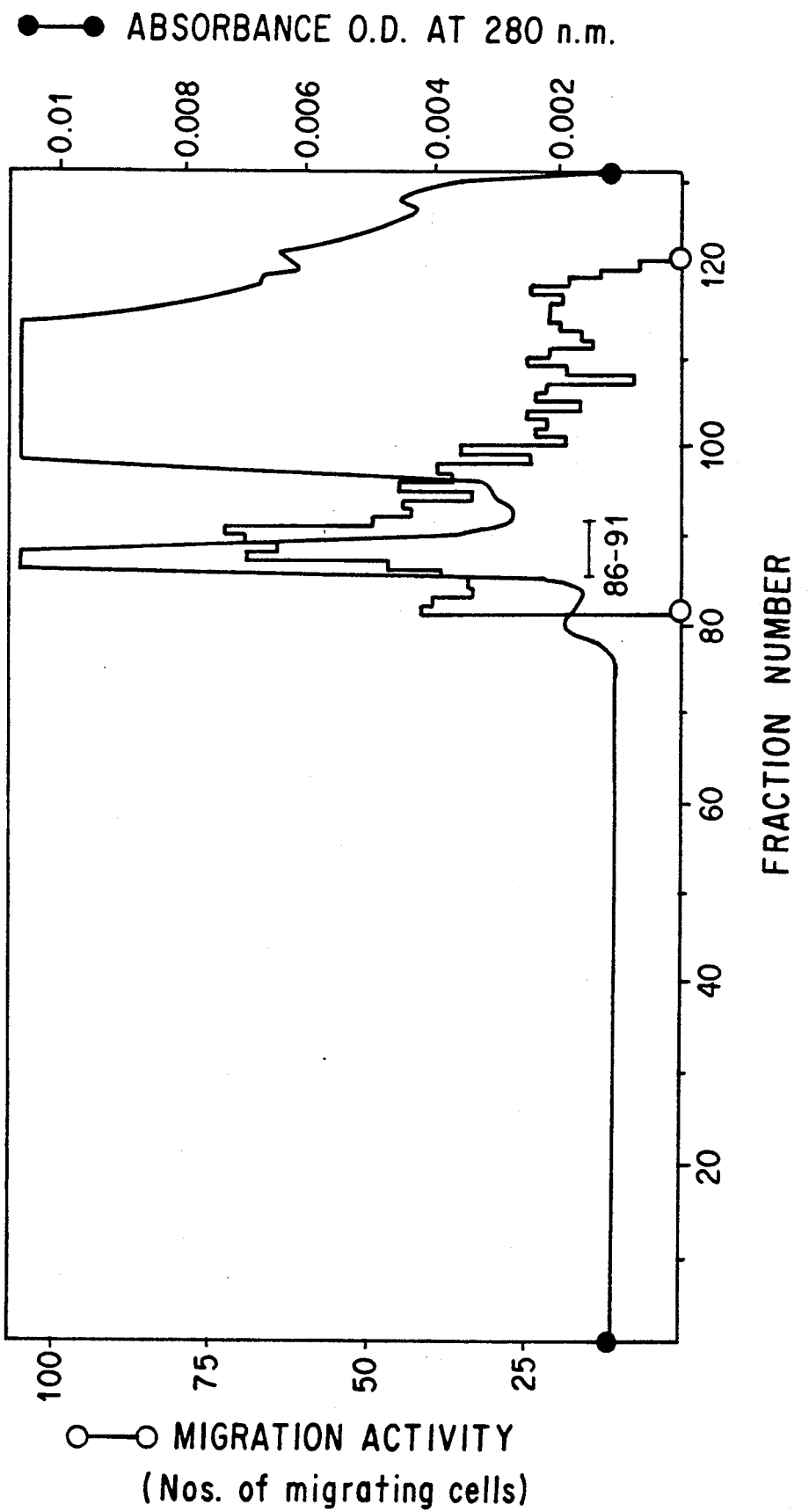
FIG. 5 represents the results of the Size-Exclusion Chromatography according to Example 1e).

The pool of the active fractions from paragraph d) (total volume usually 2-10 milliliters) is lyophilised to dryness and redissolved in 100 microliters of a buffer solution consisting of 7 parts 60% ethanol to 3 parts 2M ammonium acetate pH 5.5. The redissolved pool is then injected onto a TSK G2000 size exclusion column and an isocratic elution is performed, using the same buffer solution, at room temperature, at a flow rate of 0.2 milliliters per minute. FIG. 5 represents the absorbance at 280 nm over the entire isocratic elution phase, together with the migration activity of the collected fractions. The active fractions (Nos. 86-91) are lyophilised and stored separately at −20° C. until required.

The MGF is present in the active fractions from paragraph e) in a form which is up to, and including, 100% pure, and has a molecular weight of approximately 25000. These criteria being estimated from silver-stained SDS-PAGE gels (containing 15% acrylamide) 1.5 millimeters thick which were scanned at 530 nm against α-chymotrypsinogen standards, on a Shimadzu CS-930 dual wavelength scanning densitometer. Silver staining is performed according to Bürk, R. R. et al., Methods in Enzymology, 91, 247-254 (1983). Under flat bed iso-electric focussing conditions the activity was recovered from fractions at pH 9.0 to 10.5.

Example 2: Isolation of MGF from other fresh milk source

An appropriate quantity of fresh milk from another mammalian source, for example human, sheep or goat, is firstly diluted as in step 1a) cation exchange chromatography, hydrophobic Interaction chromatography and size exclusion chromatography are performed in analogy to Examples 1a) to 1e) whereupon a Milk Growth Factor (MGF) is obtained.

Example 3: Isolation of MGF from dried skimmed bovine milk powder

Commercially available dried skimmed bovine milk powder (25-50 kilogrammes) is washed by suspending it in 50-100 liters of acetone stirring for one hour at 20° C. and drying the washed powder overnight at room temperature in a large vacuum chamber. Less than 100 grammes of dry material is lost in the acetone and is discarded. The acetone washed powder may be kept at room temperature until used. The acetone washed milk powder (25-50 kilogrammes) is added to 250-500 liters distilled water at 4° C., stirred gently to avoid frothing for 1 hour, and the mixture is adjusted from about pH 6.7 to pH 7.0 with 1N sodium hydroxide. Further dilution of the washed and reconstituted milk powder, cation exchange chromatography, hydrophobic interaction chromatography, and size exclusion chromatography are performed in analogy to Examples 1a) to 1e) whereupon a bovine Milk Growth Factor is obtained.

Example 4: Cream (O/W-type)

| Ingredients: | % |
| --- | --- |
| Sorbitan monostearate | 2.0 |
| Polyoxyethylene sorbitan monostearate | 3.0 |
| Cetyl alcohol | 5.0 |
| Light liquid paraffin | 8.0 |
| Isopropyl myristate | 2.0 |

-continued

| Ingredients: | % |
|---|---|
| Active substance, MGF | $1.0 \cdot 10^{-5}$ |
| Propylene glycol | 2.0 |
| Glycerin | 2.0 |
| Deionised water | 76.0 |
| Preservatives and other stabilizers | q.s. |

Heat the aqueous phase to 55°–60° C., dissolve the active substance in it, and disperse the melted lipid phase in it by vigorous stirring. Cool to room temperature and homogenize.

In a similar manner a cream comprising 0.4, 4 or 20 µg/ml, respectively, can be produced.

Of this cream 100 µl/cm² of wound is applied.

Example 5: Ointment (W/O-type)

| Ingredients: | % |
|---|---|
| Sorbitan trioleate | 5.0 |
| Wax, microcrystalline | 3.0 |
| Light liquid paraffin | 9.0 |
| Isopropyl myristate | 10.0 |
| Lanolin alcohols | 3.0 |
| Active substance, MGF | $1.0 \cdot 10^{-5}$ |
| Propylene glycol | 2.0 |
| Glycerin | 2.0 |
| Magnesium sulphate, hydrous | 0.7 |
| Deionised water | 65.3 |
| Preservatives | q.s. |

Dissolve the active substance in the aqueous phase, with gentle heating, and disperse the solution in the melted lipid phase. Cool to room temperature and homogenize.

In a similar manner an ointment comprising 0.4, 4 or 20 µg/ml, respectively, can be produced. Of this ointment 100 µl/cm² of wound is applied.

Example 6: Mouthwash

| Ingredients: | % |
|---|---|
| Active substance, MGF | $1.0 \cdot 10^{-3}$ |
| Polyethyleneglycol(7)-glyceryl cocoate | 4.0 |
| Deionised water | 13.0 |
| Glycerin 86% | 18.0 |
| Peppermint oil | 10.0 |
| Ethanol | 55.0 |

Dissolve the active substance in deionised water. Add and dissolve PEG(7)-glyceryl cocoate and glycerin in the solution. Dissolve peppermint oil in ethanol and mix the two solutions with stirring. The solution is to be diluted up to 1:10 before use.

Example 7: Parenteral Solution

| Ingredients: | |
|---|---|
| Active Substance, MGF | 1 mg/ml |
| ± Human Serum Albumin | 1 mg/ml |
| Arginine or Glycine | 20 mg/ml |
| ± Carbohydrate | 5–20 mg/ml |
| pH | 7 |

The carbohydrate is glucose, mannose, dextran, hydroxyethyl starch or a mixture thereof.

The pH is adjusted with phosphate, succinate, amino acids or a mixture thereof.

Vials with 0.5 mg MGF/0.5 ml are made and lyophilised.

Example 8: Tooth paste

| | |
|---|---|
| Active Substance (MGF) | $1.0 \cdot 1.0^{-5}$ g |
| Methyl cellulose | 0.8 g |
| Calcium carbonate | 30.0 g |
| Colloidal silica | 3.0 g |
| Light liquid paraffin | 2.0 g |
| Glycerin | 20.0 g |
| Sweetening agent | |
| Flavouring agent | |
| Preservatives | |
| Deionised water to | 100.0 g |

The powders are wetted with the mixture of the active substance and methyl cellulose in a part of deionised water, paraffin and glycerin. The additives are added in solution. After making up with the remaining water the paste is homogenized.

The following protocols demonstrate that the compositions according to this invention are effective in vivo and that MGF can be employed cross-species.

Wound Healing in 10 Months Old Rats, Protocol I

In vivo activity of bovine MGF was determined by a method based on the protocols described by Zimmerli et al., (1982) J.Infect.Dis. 146: 487 and Sporn, M. B. et al., (1983) Science 219:1329.

Empty rigid polymethylacrylate or polytetrafluoroethylene tubes (internal and external diameters, 10 and 12 millimeters, respectively; length 32 millimeters), each perforated by approximately 250 regularly spaced holes (diameter 1 millimeter) and sealed at each end with a cap of identical material, were gas sterilized and surgically inserted subcutaneously, in symmetrical fashion, into the dorsal flank of fully anaesthetized Wistar Rats (approximately 10 months old). One gas-sterilized tissue cage was implanted into each flank and the incision was closed with metal clips which were removed 5 days after surgery. Following surgical insertion the chambers become encapsulated with fibrous connective tissue although there is a relative absence of cells within the chambers themselves. This model therefore presents us with a sterile, defined and enclosed space (within the implanted chamber) where a wound healing response can be quantitated. The rats were used for experimentation two weeks after implantation of the tissue cages, after full healing of the incision. At this time daily injections of MGF (0.1 millimeters, in sterile histidine buffered saline (HBS)/0.5% 'Klucel ©' vehicle buffer) were started directly into the left side chamber (chamber A). Daily doses were either 1000, 100 or 10 nanogrammes of MGF per chamber. The specific activity of the MGF was approximately $10^7$ units per milligramme as determined by a dose response assay using Balb/C 3T3 fibroblasts.

To activate MGF activity, a small amount (20 nanogrammes) of murine EGF was included in all MGF injections unless otherwise stated. Right side contralateral chambers (chamber B) were used as placebo controls and were injected with either vehicle buffer alone, or vehicle buffer containing an amount of bovine serum albumin (BSA) such that the total protein was equivalent to the amount of MGF injected into the left side chamber. Injections were made once daily for 5 days and all injected materials were sterile, endotoxin-free and pyrogen-free. All rats were individually caged for the duration of the experiment. Rats were sacrificed 6 hours after the last series of injections and all the chambers were then removed from the animals, using aseptic technique. Fibrotic material in the chambers was 'wet' weighed and the total protein in the serous chamber fluid was measured by the method of Lowry et al., J.Bio.Chem. 193, 265 (1951). Sterility of the chamber contents was checked by incubation of samples on Brain/Heart Infusion plates for 72 hours at 37° C. Statistical analysis of the data was made by comparison of matched pairs of the chambers (A v B).

Table 1 shows that daily injections of MGF, for 5 days, significantly enhanced (up to 3 fold) the accumulation of total fibrous material, in a dose-dependant manner, in left-sided chambers as compared to the right side contralateral control chambers which received placebo treatments only (Expts. 1-3).

EGF, although serving as an activating agent, had no significant effect alone, on the level of total fibrous material found in the relevant chambers (Expt. 4). MGF also significantly enhanced the amount of total serous fluid protein in the left-sided chambers as compared to the contralateral right-sided chambers which received placebo treatments only (Expts. 1-3). Again EGF had little effect alone on the levels of total serous fluid protein in relevant chambers (Expt. 4).

right-side control chambers under predominance of macrophage populations in left-side chambers which had received MGF in Expts. 1-3. The contents of all 40 chambers in Expts. 1-4 were proved to be sterile after incubating samples of the contents of each chamber on brain heart infusion for 72 hours at 37° C.

Wound Healing in over 480 Days Old Mice, Protocol II

It has long since been noticed, but tested only recently, that the wound healing process becomes impaired with advancing age (Grove, G. L. (1982) Arch-.Dermatol.Res. 272:381) and as such represents a major problem in geriatric medicine. It was therefore decided to investigate the effects of bovine MGF on a wound-healing response, using partial-thickness wounding (by second degree burning) in a partially deficient or impaired wound healing situation, nameiy in old animals, using a similar protocol described by Schultz, G. S. et al., (1987) Science 235:350. Single middermal thermal injuries were made on the dorsal thorax of anaesthetized, aged (480 to 600 days) C57/BL6 mice, whose backs had been previously shaved and depilitated with a commercial cream-type hair remover, by a single application, for 10 seconds, of a brass template (1×1 cm, 8 gm) which had been equilibrated at 80° C. in a water bath. The resulting blister was surgically re-

TABLE 1

| | | | | (rats, ~10 months old) | | | | | | |
|---|---|---|---|---|---|---|---|---|---|---|
| | Treatment | | Number of matched | Total amount of fibrous material (mg) in | | Average ratio of material in Chamber A to | | Total Amount of protein in serous fluid (mg.) | | |
| Expt. | Chamber A | Chamber B | pairs | Chamber A | Chamber B | Chamber B | P | Chamber A | Chamber B | P |
| 1 | 1.0 μg MGF + 20 ng EGF | 1.0 μg BSA | 5 | 453.0 ± 110.8 | 169.6 ± 32.2 | 2.7 ± 0.5 | <.001 | 34.4 ± 2.7 | 22.6 ± 4.7 | <.0005 |
| 2 | 100 ng MGF + 20 ng EGF | 100 ng BSA | 5 | 336.8 ± 35.1 | 151.0 ± 16.9 | 2.3 ± 0.3 | <.0005 | 35.5 ± 9.5 | 27.1 ± 9.0 | <.001 |
| 3 | 10 ng MGF + 20 ng EGF | 10 ng BSA | 5 | 294.0 ± 33.1 | 143.0 ± 28.6 | 2.1 ± 0.3 | <.0005 | 24.5 ± 5.6 | 17.2 ± 1.9 | <.025 |
| 4 | 20 ng EGF | — | 5 | 127.1 ± 31.1 | 125.8 ± 23.0 | 1.0 ± 0.2 | NS | 20.9 ± 9.7 | 19.6 ± 7.3 | NS |

At the end of experiments 1-3 it was consistently observed, at post-mortem biopsy, that the left sided MGF-treated chambers were more firmly fixed to the surrounding connective tissues of the body wall than the respective matched control chambers, and that the thickness of the fibrotic material immediately surrounding the MGF-treated chambers was markedly greater than that surrounding the respective matched control chambers. This observation would suggest that the effects of MGF are also manifest in the area immediately surrounding the respective chambers. No apparent differences in the thickness of fibrotic material surrounding the chambers was observed in Expt. 4. The contralateral chambers also show dose dependent small increases over the control which might be explained by transmission through the circulation of MGF to this chamber.

Histological preparations revealed the extent of the enhanced tissue-thickness and vascularity around the MGF-treated left side chambers in Expts. 1-3, and also the occurrence of fibroblast proliferation within the contents of the fibrous granulation tissue inside each chamber. A sterile infiltrate of inflammatory cells was found in the serous fluid of both treated and control chambers although differential counts showed a slight predominance of polymorphonuclear leukocytes in moved and the burns were treated daily, for 5 days, with a topical application of 25 μl sterile vehicle buffer containing various amounts of MGF (500 nanogrammes, 100 nanogrammes or 10 nanogrammes; specific activity of the MGF was approximately $10^7$ units per milligramme as determined by a dose response assay using Balb/C 3T3 fibroblasts) in the presence of a constant small amount (20 nanogrammes) of murine EGF, or were left untreated. All materials for topical application were sterile, endotoxin free and pyrogen free, and all mice were individually caged for the duration of the experiments.

After 5 days of treatment with MGF, the mice were anaesthetized, the blisters (if present) were surgically removed from the burns, and the burns were photographed. Areas of burns that had regenerated epithelium were outlined onto uniform thickness transparent plastic film ('Scotch'© overhead projector film) and the percentage of the original burn area that had healed was measured by planimetry. Values shown in Table 2 are the mean and range of the group evaluations. Results were also compared with the epithelial regeneration process in young (56-84 day old C57/BL6 mice with identical middermal burns but which were left untreated for the duration of the experiment. All mice were individually caged and experimental groups consisted of 5 mice per group.

TABLE 2

(mice, over 480 days old)

| Expt. | Animals | Treatment | Gp. | % age of original burn area remaining on day 6 |
|---|---|---|---|---|
| 1 | Old | 500 ng MGF + 20 ng EGF | A | 45 ± 9 |
| 2 | Old | 100 ng MGF + 20 ng EGF | B | 51 ± 7 |
| 3 | Old | 10 ng MGF + 20 ng EGF | C | 54 ± 5 |
| 4 | Old | 20 ng EGF | D | 78 ± 5 |
| 5 | Old | Vehicle | E | 91 ± 5 |
| 6 | Old | N.T. | F | 90 ± 6 |
| 7 | Young | N.T. | G | 36 ± 7 |

Table 2 shows the results of the planimetrical analyses and deemonstrates that topical application of MGF, daily for 5 days, in a suitable vehicle buffer and in the presence of a small amount of murine EGF, stimulated and accelerated epithelial regeneration in old mice in a dose-dependant fashion (Expts. 1-3) when compared with EGF only, vehicle only or untreated wounds (Expts. 4-6 respectively) young mice were apparently competent enough to successfully re-epithelialize their wounds in the absence of any topically applied MGF (Expt. 7).

Histological analyses of the experimentally-induced wounds in this series of experiments revealed their extension to (and possibly including) the basal (germinative) layer of the epidermis. Such wounds heal by first intent in a process involving the division and migration of cells in both the vertical and lateral planes, and one which results not only in the re-epithelialisation and reclosure of the wound, but one which later produces a thickening or hyper-keratosis of the regenerated epidermis. Histological analyses also revealed the extent of the enhancement (or acceleration) of this re-epithelialisation process in animals which had been treated with MGF (Expts. 1-3) and a relative absence of new epithelia in any of the control groups (Expts. 4-6). Young animals also showed a marked re-epithelialisation of their wounds (Expt. 7).

The results of a similar experiment with 100 ng of MGF, a mixture of 100 ng of MGF and 100 ng of EGF, 100 ng of EGF alone, vehicle alone, untreated old mice and untreated young mice are compiled in Table 3.

TABLE 3

| Group | Animal | Treatment | Percentage of original burn area remaining on day 6 |
|---|---|---|---|
| 1 | Old | 100 ng MGF | 46 ± 9 |
| 2 | Old | 100 ng MGF + 100 ng EGF | 41 ± 5 |
| 3 | Old | 100 ng EGF | 76 ± 9 |
| 4 | Old | vehicle only | 78 ± 5 |
| 5 | Old | untreated | 81 ± 9 |
| 6 | Young | untreated | 34 ± 5 |

Table 3 showing epithelial regeneration of partial-thickness burns in groups of old C57BL/6J mice which has been treated daily, for 5 days, with a viscous vehicle buffer containing MGF in the presence or absence of EGF. Each group consisted of 5 animals. The values reported are the mean and range of 3 individual evaluations for each wound.

Wound Healing in Old Pigs, Protocol III:

Two healthy 'old' large white sows (aged from 7-8 years; weight 250-300 kg) together with two healthy 'young' female pigs (aged from 2-3 months; weight 25-30 kg) of the same breed, were selected and restrained separately in tight holding boxes for the duration of the experiment in order to prevent the animals from licking their wounds or lying on them. Since pigs are usually disposed of before the end of their normal lifespan (sows being seldom kept under husbandry conditions for longer than 4 years) the average lifespan, for both the species and the breed, kept as a laboratory animal, is unknown although old sows have been known to produce litters at 10 years and reach 15-20 years of age. Pigs were chosen as suitable models for partial-thickness wounding in man because of the similarities in epidermal structure, morphology and the rate of cell turnover.

All animals were shaved and depilitated using a commercial hair remover cream prior to wounding.

Pigs were given full surgical anaesthesia prior to multiple wounding. As a sedative, Azaperone (STRESNYL ©, Janssen, Beerse, Belgium; 1 mg.kg$^{-1}$) was administered to each pig intravenously through the central ear vein, followed 20 minutes later with Metomidate Hydrochloride (HYPNODIL ©, Janssen; Beerse, Belgium; 4 mg.kg$^{-1}$) by the same route.

A brass template (3×3 cm; 78 g) was equilibrated to 90° C. in a water bath, placed in firm contact with the depilitated dorsal surface of the skin for exactly 10 seconds to produce multiple, partial-thickness burns of each animal and the resulting blister removed.

The multiple partial-thickness burns on the dorsal thorax of old pigs were treated daily for 9 days with 225 μl of vehicle buffer containing either MGF (4.5 μg, 0.9 μg or 0.45 μg), EGF (4.5 μg, 0.9 μg or 0.45 μg) or equal combinations of both factors (4.5 μg MGF+4.5 μg EGF, 0.9 μg MGF+0.9 μg EGF, 0.45 μg MGF+0.45 μg EGF). These dosages were chosen so that the pigs received the same amount of material, per square centimeter of wound surface area, as did the mice in a previous experiment. Control burns on each animal received either vehicle-only treatments or were left untreated. As a further control, two young pigs each received similar single partial-thickness burns which were also left untreated for the duration of the experiment. The degree of re-epithelialization for each burn was assessed on the 10th day by planimetry and by histological examination of a limited amount of biopsy material. Table 4 shows the results of the planimetrical analyses. The normal re-epithelialisation of untreated wounds was markedly better in young pigs (Treatment 12) than in older ones (Treatment 11) over the 10 day experimental period. As in the previous experiments a daily topical appication of MGF, either in the presence or absence of EGF, markedly improved this repair process in the older animal (Treatments 1-6) to such an extent that the levels of re-epithelialisation again resembled those seen in young animals with untreated wounds (Treatments 12). Daily application of Vehicle Buffer (Treatment 10) or EGF over a concentration range 100-500 ng cm$^{-2}$ burn area (Treatments 7-9) had little effect on the re-epithelialisation process in old pigs.

Light microscopy of biopsy material confirmed the results of the planimetrical analyses and revealed a thin epidermis, consisting of as few as two distinct epthelial cell layers, in the intact zone surrounding each wound and also the enhancement of the re-epithelialisation process in wounds that had been treated with MGF, (either in the presence or absence of EGF). Although there was no visible evidence of any metaplasia in the newly regenerating epithelia, a slight but distinct hyperkeratosis was apparent in all groups of mice at the perimeter of each wound. Another general observation was that wounds treated with MGF (either in the presence or absence of EGF) appeared to contain more granulation tissue, mostly subjacent to the newly regenerated epidermis, than wounds which had remained untreated or had received EGF-only or vehicle-only treatments. In general, similar observations were seen in the limited amount of biopsy material available from the pig study although the structural appearance of the intact epidermis surrounding the wounds in old animals more closely resembled the well defined, multi-layered arrangement that is characteristic of the younger animal.

TABLE 4

(Old pigs)
Showing Epithelial Regeneration of partial-thickness burns in 2 old large white sows treated daily for 9 days with a viscous vehicle buffer containing MGF in the presence or absence of EGF. The values reported are the mean and range of 3 individual evaluations for each wound.

| Animals | Expt. Number | Treatment + | Percentage of original burn area remaining on day 10 | |
|---|---|---|---|---|
| | | | Animal 1 | Animal 2 |
| Old | 1. | 4.5 µg MGF | 7 ± 4 | 10 ± 2 |
| Old | 2. | 0.9 µg MGF | 10 ± 2 | 12 ± 4 |
| Old | 3. | 0.45 µg MGF | 15 ± 6 | 15 ± 5 |
| Old | 4. | 4.5 µg MGF + 4.5 µg EGF | 9 ± 2 | 18 ± 4 |
| Old | 5. | 0.9 µg MGF + 0.9 µg EGF | 18 ± 2 | 20 ± 2 |
| Old | 6. | 0.45 µg MGF + 0.45 µg EGF | 17 ± 4 | 21 ± 5 |
| Old | 7. | 4.5 µg EGF | 26 ± 4 | 29 ± 2 |
| Old | 8. | 0.9 µg EGF | 28 ± 3 | 36 ± 3 |
| Old | 9. | 0.45 µg EGF | 29 ± 2 | 37 ± 4 |
| Old | 10. | Vehicle-only | 31 ± 6 | 37 ± 5 |
| Old | 11. | untreated | 42 ± 6 | 40 ± 6 |
| Young | 12. | untreated | 8 ± 2 | 7 ± 3 |

The results shown in Protocols I to III indicate that MGF can significantly accelerate and enhance the wound healing, by first and second intent, in vivo, whereas in both of the examples, placebo treatments or activating agent alone failed to produce such a response.

Cellular Immune Response, Protocol IV

One way mixed leukocyte reaction (MLR): Lymphocytes from two different strains of mice (CBA and Balb/c) were mixed together in vitro in TC 96 plate wells ($2 \times 10^5$ cells, from each strain per well; CBA lymphocytes were 'responders', and irradiated Balb/c lymphocytes were 'stimulators') and the proliferative response was measured after 72 hours by $^3$H-thymidine incorporation.

Result: $\simeq$1000 pg.ml$^{-1}$ of MGF caused 50% inhibition of proliferation.

Cloned T-cell assay (mouse): A mouse long term T-cell clone specific for a soluble antigen (arsenate-tyrosine) was incubated in vitro in TC 96 plate wells ($10^5$ cells per well) with mouse peritoneal macrophages ($2 \times 10^5$ cells per well) previously pulsed with antigen. T-cell proliferation and production of interferon-$\gamma$ was measured after 72 hours.

Result: $\simeq$500 pg.ml$^{-1}$ of MGF caused 50% inhibition of both proliferation and IFN-$\gamma$ release.

Murine lymphocyte assay: Unprimed murine lymphocytes were stimulated in vitro in TC 96 plate wells ($10^5$ cells per well) with lipopolysaccharide (LPS, 2, 5 µg per well) and the proliferative response was measured after 72 hours by $^3$H-Thymidine incorporation.

Result: $\simeq$1000 pg.ml$^{-1}$ of MGF caused 50% inhibition of proliferation in this assay.

Human T-lymphocyte Assay: Unprimed human T-lymphocytes were stimulated in vitro in TC 96 plate wells ($10^5$ cells per well) with either a) phytohaemagglutinin A (PHA, 0,5%) b) anti-T3 antibody plus Phorbol Ester (PDBu, 1 ng ml$^{-1}$), or c) ionomycin (0.25 µg ml$^{-1}$) plus PDBu (10 ng ml$^{-1}$). Proliferative responses were measured after 72 hours by $^3$H-thymidine incorporation.

Result: a) $\simeq$10 pg ml$^{-1}$ of MGF caused 50% inhibition of proliferation b) $\simeq$1 pg ml$^{-1}$ of MGF caused 50% inhibition of proliferation b) $\simeq$10 pg ml$^{-1}$ of MGF caused 50% inhibition of proliferation.

Antigen Specific Human T-Lymphocyte Assay: Freshly isolated human T-lymphocytes were stimulated in vitro in TC 96 plate wells ($10^5$ cells per well) with a specific antigen, tetanus toxoid, and the proliferative response was measured by $^3$H-thymidine incorporation.

Result: $\simeq$50 pg ml$^{-1}$ of MGF caused 50% inhibition of proliferation.

Cloned T-Cell Assay (Human)

A human, long term T-cell clone (T4+/T8−) specific for a soluble antigen, purified protein derivatives from mycobacteria (PPD), was incubated in vitro in TC 96 plate wells ($2 \times 10^4$ cells per well) with either:
a) isologous human monocytes ($10^5$ cells per well) which had been previously pulsed with antigen
or b) with isologous cells from an Epstein Barr Virus (EBV)—transformed B cell line ($8 \times 10^4$ cells per well).

Proliferative responses were measured after 72 hours by $^3$H-thymidine incorporation.

Results: a) $\simeq$500 pg ml$^{-1}$ of MGF caused 50% inhibition of proliferation
b) $\simeq$10 ng ml$^{-1}$ of MGF caused 50% inhibition of proliferation.

Il-2 Driven Proliferation of Human ConA Lymphoblasts

Human concanavalin A (ConA) lymphoblasts were incubated in vitro in TC 96 plate wells ($10^4$ cells per well) in the presence of recombinant interleukin 2 (rIl-2, 3 or 9 ng ml$^{-1}$) and the proliferative response was measured after 96 hours by $^3$H-thymidine incorporation.

Result: $\simeq$0.1 pg ml$^{-1}$ of MGF caused 50% inhibition of proliferation.

Il-4 Driven Proliferation of Human T Lymphocytes

Unprimed human T lymphocytes (>95% T3+) were incubated in vitro in TC 96 plate wells ($10^5$ cells per well) in the presence of PDBu (10 ng ml$^{-1}$) plus recombinant interleukin 4 (rIl-4, 10 ng ml$^{-1}$) and the proliferative response was measured after 72 hours by $^3$H-thymidine incorporation.

Result: $\simeq$500 pg ml$^{-1}$ of MGF caused 50% inhibition of proliferation.

Humoral Immune Response, Protocol V

Mice were primed in vivo with a hapten-carrier conjugate (Dinitrophenyl-chicken gamma globulin; DNP-CGG, 200 μg per mouse). Two months later spleen cells were challenged in vitro in TC 96 plate wells ($3 \times 10^5$ cells per well) with DNP-CGG (10 ng-100 ng per well) and the number of antihapten (DNP) antibody forming cells were determined after 4 days by a Jerne plaque test.

Result: $\simeq 50$ pg.ml$^{-1}$ of MGF caused 50% inhibition of antibody forming B-cells. $\simeq 1000$ pg.m.$^{-1}$ of MGF also caused 50% inhibition of proliferation.

Tumour Cell Lysis, Protocol VI

MAF ASSAY: Adherent human monocytes in TC 96 plates were stimulated for 24 hours with different concentrations of MGF. After washing the monocytes once, Melanoma A375 target cells were added. Controls included macrophages and tumour cells alone, a mixture of non-stimulated macrophages with target cells, the Klucel solvent (see Protocol I) and MAF standards.

After 72 hours incubation the cell monolayers were washed once, fixed and stained with crystalviolet for 15 min. Unbound stain was washed out intensively. The remaining stained cells were lysed with acetic acid and the OD was measured at 590 nm with a Multiskan-8 Channel Photometer equipped with an Olivetti M24 PC to calculate the activity of the test compounds. Data are expressed as ED$_{30}$.

Results: MGF treatment stimulated the monocytes to tumour cytolytic activity. The ED$_{30}$ was found at the concentration. $0.17 \pm 0.14$ ng.ml$^{-1}$ (n=4 experiments).

The Klucel controls were inactive.

Cytotoxicity for proliferating Melanoma A375 cells

MGF was diluted in C-RPMI medium+5% FCS in TC 96 plates. Controls were medium alone, and Klucel. (100 ng MGF were dissolved in 50 μl Klucel and then diluted with C-RPMI medium+5% FCS). $1.2 \times 10^4$ A375 target cells were added in each well. After a 72-hour incubation at 37° C. in 5% CO$_2$ the A375 tumour cell monolayers were stained and the cytotoxic activity was calculated with the same procedure as described for the MAF assay.

Results: MGF was cytotoxic for proliferating melanoma A375 tumour cells. The ED$_{30}$ was found at the concentration $0.18 \pm 0.12$ ng.ml$^{-1}$ (n=4 experiments).

These experiments indicate that the MGF concentrations stimulating monocytes to tumour cytolysis and the direct tumour cytotoxic activity are very close ($0.17 \pm 0.14$ versus $0.18 \pm 0.12$).

Growth inhibition of Estradiol-dependant and Estradiol-independant human breast cancer cell lines. Protocol VII Two human mammary carcinoma cell lines with estradiol receptors, MCF-7 and ZR-75-1, and one human mammary carcinoma cell line without measurable estradiol receptors, MDA-MB-231, were seeded separately in TC96 plates at a density of $3-6 \times 10^3$ cells per well and stimulated with different concentrations of MGF in Klucel solvent (see Protocol I). Controls included carcinoma cells alone and carcinoma cells cultured in the presence of Klucel solvent only. After 8-10 days incubation under defined serum-free conditions the adherant cell monolayers were washed and then fixed and stained with crystal violet for 15 minutes. Any unbound stain was washed out extensively and since the bound stain was confined to the nucleus, this technique provided a colorimetrical assay for measuring cell growth and proliferation. The O.D. was measured at 590 nm with a Multi-skan 8 Channel Photometer equipped with an Olivetti M24 PC to calculate the activity of the test compounds on carcinoma cell growth over the experimental period.

Results: Treatment with MGF, over a concentration range $10^{-9}$-$10^{-13}$M, inhibited the growth of both estradiol-dependant cell lines MCF-7 and ZR-75-1, and the estradiol-independant cell line MDA-MB-231, when compared with untreated control cells. Klucel solvent has no effect on any of the cell lines in this assay.

What is claimed is:

1. A process for the preparation of Milk Growth Factor (MGF) having a molecular weight of about 25 kd as determined by SDS-PAGE, or a salt thereof, comprising subjecting a milk or milk product containing MGF to a polypeptide separation technique comprising, in sequence, cation exchange chromatography, hydrophobic interaction chromatography, and size exclusion chromatography, and separating the resulting MGF or MGF salt containing fraction.

2. The process of claim 1 further comprising transforming the resulting free MGF into a salt thereof.

3. The process of claim 1 further comprising transforming the resulting salt form of MGF into free MGF.

4. The process of claim 1 further comprising subjecting said MGF fraction of a technique selected from the group consisting of countercurrent distribution, electrofocussing, chromatofocussing, dialysis, salt and solvent precipitation, gel adsorption, cellulose ion exchange chromatography, electrophoresis chromatography on porous glass beads, and chromatography on immobilized zinc chelate HPLC.

5. The process of claim 1 wherein a Dowex AG 50W X2 50–100 mesh resin and an elution buffer consisting of 700 mM potassium acetate solution and ethanol in a 60:40 ratio at pH 7.6 is used in said cation exchange chromatography.

* * * * *